(12) United States Patent  (10) Patent No.: US 7,771,483 B2
Justin et al.  (45) Date of Patent: Aug. 10, 2010

(54) TIBIAL CONDYLAR HEMIPLASTY IMPLANTS, ANCHOR ASSEMBLIES, AND RELATED METHODS

(75) Inventors: Daniel F. Justin, Logan, UT (US); E. Marlowe Goble, Alta, WY (US); Joel Dever, Nibley, UT (US); Carlyle J. Creger, Logan, UT (US); Daniel J. Triplett, Providence, UT (US)

(73) Assignee: Zimmer, Inc., Warsaw, IN (US)

( * ) Notice: Subject to any disclaimer, the term of this patent is extended or adjusted under 35 U.S.C. 154(b) by 18 days.

(21) Appl. No.: 10/749,346

(22) Filed: Dec. 30, 2003

(65) Prior Publication Data

US 2005/0143831 A1   Jun. 30, 2005

(51) Int. Cl.
*A61F 2/38* (2006.01)
(52) U.S. Cl. .................................... 623/20.34
(58) Field of Classification Search ............. 623/20.17, 623/20.3, 20.31, 20.16, 23.14, 23.12, 23.26, 623/14.12, 11.11, 16.11, 20.14, 20.15, 20.32–20.34, 623/20.25, 20.26, 20.35, 20.36; 606/96
See application file for complete search history.

(56) References Cited

U.S. PATENT DOCUMENTS

| 4,000,525 | A |  | 1/1977 | Klawitter et al. |
| 4,224,696 | A |  | 9/1980 | Murray et al. |
| 4,479,271 | A |  | 10/1984 | Bolesky et al. |
| 4,502,161 | A |  | 3/1985 | Wall |
| 4,627,853 | A |  | 12/1986 | Campbell et al. |
| 4,657,549 | A |  | 4/1987 | Keller |
| 4,673,407 | A |  | 6/1987 | Martin |
| 4,838,891 | A |  | 6/1989 | Branemark et al. |
| 4,927,421 | A |  | 5/1990 | Goble et al. |
| 5,019,103 | A | * | 5/1991 | Van Zile et al. .......... 623/20.34 |
| 5,035,699 | A |  | 7/1991 | Coates |
| 5,037,439 | A |  | 8/1991 | Albrektsson et al. |
| 5,092,895 | A |  | 3/1992 | Albrektsson et al. |
| 5,100,409 | A |  | 3/1992 | Coates et al. |
| 5,176,684 | A |  | 1/1993 | Ferrante et al. |
| 5,282,868 | A |  | 2/1994 | Bahler |
| 5,474,559 | A |  | 12/1995 | Bertin et al. |
| 5,489,311 | A | * | 2/1996 | Cipolletti .................. 623/20.34 |
| 5,569,259 | A |  | 10/1996 | Ferrante et al. |
| 5,571,196 | A |  | 11/1996 | Stein |
| 5,593,411 | A |  | 1/1997 | Stalcup et al. |
| 5,674,224 | A |  | 10/1997 | Howell et al. |
| 5,702,397 | A |  | 12/1997 | Goble et al. |

(Continued)

FOREIGN PATENT DOCUMENTS

DE    3 917 285    11/1990

(Continued)

*Primary Examiner*—Alvin J Stewart
(74) *Attorney, Agent, or Firm*—Baker & Daniels LLP

(57) ABSTRACT

A method for mounting a tibial condylar implant includes forming a tunnel having a proximal end on a lateral, medial, or anterior side of a proximal end of the tibia and a distal end on an at least partially resected lateral or medial facet at the proximal end of the tibia. A condylar implant is positioned over the distal end of the tunnel. A fastener is advanced into the tunnel from the proximal end of the tunnel. The fastener which is at least partially disposed within the tunnel is secured to the condylar implant.

33 Claims, 27 Drawing Sheets

U.S. PATENT DOCUMENTS

| | | | |
|---|---|---|---|
| 5,702,459 A | 12/1997 | Hummer et al. | |
| 5,709,689 A | 1/1998 | Ferrante et al. | |
| 5,741,262 A * | 4/1998 | Albrektsson et al. | 606/80 |
| 5,743,915 A | 4/1998 | Bertin et al. | |
| 5,755,800 A | 5/1998 | O'Neil et al. | |
| 5,766,255 A | 6/1998 | Slamin et al. | |
| 5,769,855 A | 6/1998 | Bertin et al. | |
| 5,776,201 A | 7/1998 | Colleran et al. | |
| 5,824,098 A | 10/1998 | Stein | |
| 5,860,981 A | 1/1999 | Bertin et al. | |
| 5,879,391 A | 3/1999 | Slamin | |
| 5,968,045 A | 10/1999 | Frazier | |
| 6,068,648 A | 5/2000 | Cole et al. | |
| 6,071,311 A | 6/2000 | O'Neil et al. | |
| 6,102,954 A * | 8/2000 | Albrektsson et al. | 623/20.32 |
| 6,162,234 A | 12/2000 | Freedland et al. | |
| 6,168,629 B1 | 1/2001 | Timoteo | |
| 6,171,342 B1 | 1/2001 | O'Neil et al. | |
| 6,245,110 B1 * | 6/2001 | Grundei et al. | 623/20.31 |
| 6,319,271 B1 | 11/2001 | Schwartz et al. | |
| 6,368,326 B1 | 4/2002 | Dakin et al. | |
| 6,461,373 B2 | 10/2002 | Wyman et al. | |
| 6,520,964 B2 | 2/2003 | Tallarida et al. | |
| 6,544,267 B1 | 4/2003 | Cole et al. | |
| 6,554,838 B2 | 4/2003 | McGovern et al. | |
| 6,610,067 B2 | 8/2003 | Tallarida et al. | |
| 6,652,587 B2 | 11/2003 | Felt et al. | |
| 6,679,917 B2 | 1/2004 | Ek | |
| 6,736,819 B2 | 5/2004 | Tipirneni | |
| 6,866,683 B2 * | 3/2005 | Gerbec et al. | 623/18.11 |
| 6,905,514 B2 | 6/2005 | Carignan et al. | |
| 6,994,725 B1 | 2/2006 | Goble | |
| 7,250,061 B2 | 7/2007 | Jacobsson et al. | |
| 2002/0055783 A1 | 5/2002 | Tallarida et al. | |
| 2002/0138150 A1 | 9/2002 | Leclercq | |
| 2002/0147498 A1 | 10/2002 | Tallarida et al. | |
| 2002/0198528 A1 | 12/2002 | Engh et al. | |
| 2003/0033018 A1 | 2/2003 | Merchant | |
| 2003/0060887 A1 | 3/2003 | Ek | |
| 2003/0120276 A1 | 6/2003 | Tallarida et al. | |
| 2003/0158606 A1 | 8/2003 | Coon et al. | |
| 2003/0225456 A1 | 12/2003 | Ek | |
| 2003/0225457 A1 | 12/2003 | Justin et al. | |
| 2004/0015170 A1 | 1/2004 | Tallarida et al. | |
| 2004/0106928 A1 * | 6/2004 | Ek | 606/96 |
| 2004/0148030 A1 | 7/2004 | Ek | |
| 2005/0137708 A1 | 6/2005 | Clark | |
| 2005/0143831 A1 | 6/2005 | Justin et al. | |
| 2005/0149044 A1 | 7/2005 | Justin et al. | |
| 2005/0154398 A1 | 7/2005 | Miniaci et al. | |
| 2005/0177242 A1 | 8/2005 | Lotke | |

FOREIGN PATENT DOCUMENTS

| | | |
|---|---|---|
| EP | 0 336 774 B1 | 10/1989 |
| EP | 0 714 645 B1 | 6/1996 |
| EP | 0 850 606 A2 | 7/1998 |
| EP | 0 985 386 A2 | 3/2000 |
| FR | 2 521 421 | 11/1975 |
| FR | 2 682 589 | 4/1993 |
| FR | 2 718 953 | 10/1995 |
| GB | 2 007 980 A | 5/1979 |
| WO | WO 89/09578 A1 | 10/1989 |
| WO | WO 89/11837 | 12/1989 |
| WO | WO 91/06260 | 5/1991 |
| WO | WO 01/28457 A1 | 4/2001 |
| WO | WO 01/66021 A1 | 9/2001 |
| WO | WO 01/66022 A1 | 9/2001 |
| WO | WO 03/051210 A2 | 6/2003 |
| WO | WO 03/051211 A1 | 6/2003 |
| WO | WO 03/099159 A2 | 12/2003 |

* cited by examiner

TIBIAL CONDYLAR HEMIPLASTY IMPLANTS, ANCHOR ASSEMBLIES, AND RELATED METHODS

CROSS-REFERENCE TO RELATED APPLICATIONS

Not applicable.

BACKGROUND OF THE INVENTION

1. The Field of the Invention

The present invention relates to tibial condylar hemiplasty implants, anchor assemblies used to secure such implants to the tibia, and the related methods.

2. The Relevant Technology

The knee joint comprises two generally rounded condyles, i.e., lateral and medial condyles, that are located at the lower or distal end of the femur. These femoral condyles are disposed above corresponding lateral and medial condyles located at the upper or proximal end of the tibia. A flexible meniscus provides cushioning between the opposing matching pairs of condyles.

As a result of injury, wear, disease or other causes, it is occasionally necessary to replace all or part of the knee joint. Knee replacements typically entail cutting off or resecting both of the femoral condyles and the tibial condyles. Complementary artificial implants are then mounted on the distal end of the femur and the proximal end of the tibia. Where only one condyle has been injured, more recent procedures provide for partial knee replacement. In this procedure, only one of the lateral or medial femoral condyles is resected. The corresponding one of the lateral or medial tibial condyles is also resected. Implants referred to as "unicondylar" implants are mounted on the resected area of the femur and tibia.

Although knee replacements have met with success, one of the significant drawbacks to knee replacements is the recovery. Traditional knee replacements, both full and partial, require an open procedure wherein relatively large incisions are made so as to fully expose the respective ends of the femur and tibia. This exposure is necessary when using conventional techniques to resect the femur and tibia and for mounting the implants. For example, conventional tibial implants are screwed directly into the resected end face of the tibia. Mounting such screws requires exposure of the resected end face. In yet other embodiments, projections are formed on the implants which are received within slots formed on the resected end face of the tibia. Again, forming of the slots and inserting the implant into the slots requires substantially full expose of the resected end face of the tibia.

In general, the more invasive the surgery, the more difficult and time consuming the patient recovery. Furthermore, such open and invasive surgeries have a greater risk of infection.

Accordingly, what is needed are systems and methods for resecting and mounting a condylar implant on the tibia that uses procedures that minimize incisions, the amount of bone resection, and/or the impact on soft tissue.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to methods and apparatus for preparing and mounting a condylar implant on a tibia of a patient. The methods and apparatus are designed so that the condylar implant can be mounted using procedures that are minimally invasive. As a result, recovery time is significantly improved while the risk of infection minimized.

Figure 1:
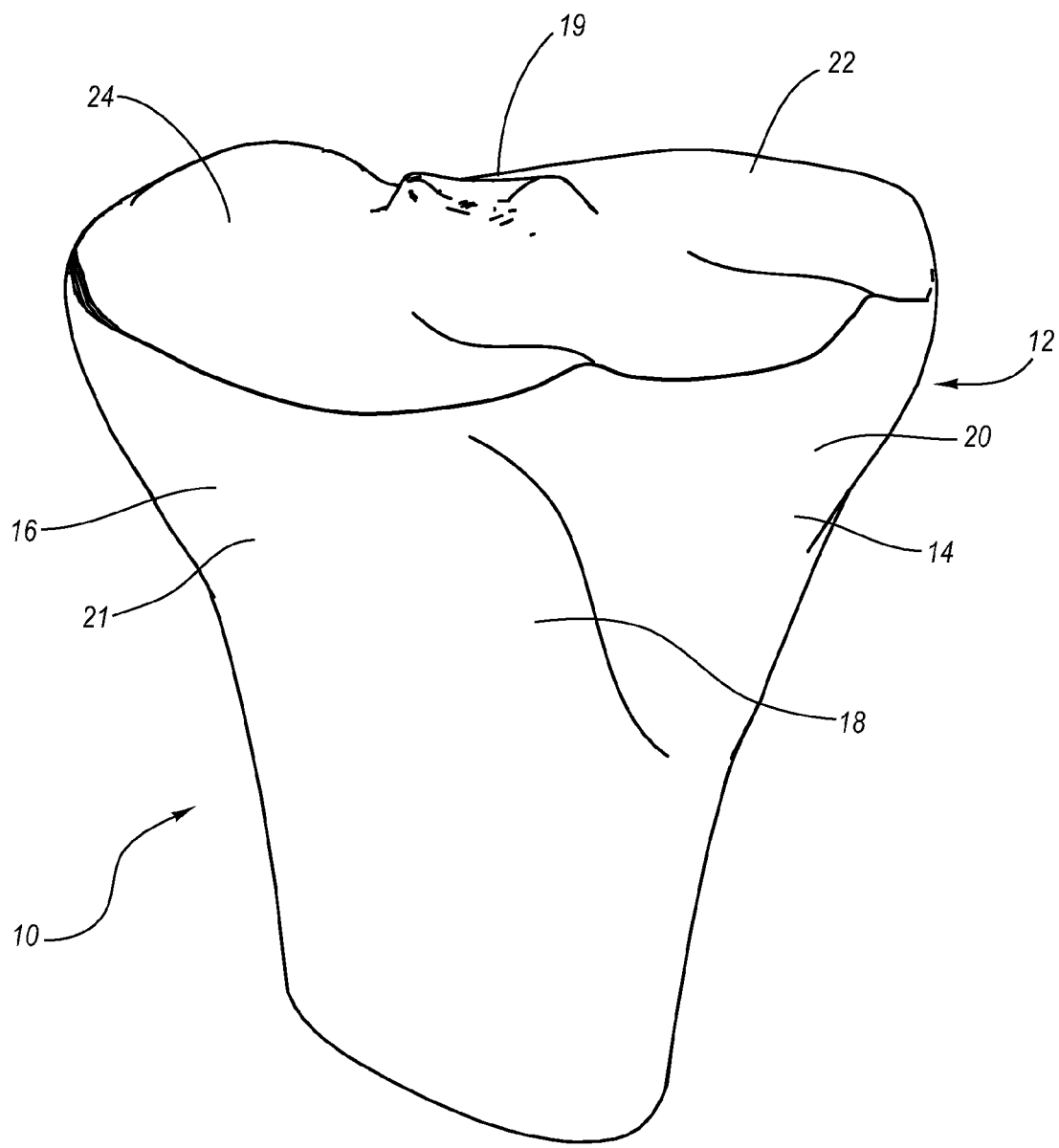
FIG. 1 is a perspective view of the proximal end of a tibia.

Depicted in FIG. 1 is a proximal end 10 of a tibia 12. Proximal end 10 has a lateral side 14 and a medial side 16 which each extend between an anterior side 18 and a posterior side 19. Proximal end 10 further comprises a lateral condyle 20 and a medial condyle 21. Lateral condyle 20 terminates proximally at a lateral facet 22 of a superior articular surface of tibia 12 while medial condyle 21 terminates proximally at medial facet 24 of a superior articular surface of tibia 12.

Although tibia 12 shown in FIG. 1 is from a left leg, it is appreciated that the tibia of the right leg has a complimentary configuration and that the methods and apparatus disclosed herein are equally applicable thereto. Furthermore, the methods and apparatus disclosed herein are primarily illustrated in association with medial condyle 21 of tibia 12. It is also appreciated that the methods and apparatus can be used in association with lateral condyle 20.

In one embodiment, to facilitate mounting of a condylar implant on medial condyle 21, conventional arthroscopic procedures are used to resect the posterior portion of the medial meniscus. Once the posterior portion of the medial meniscus is removed, a vertical or horizontal incision, generally in a range between about 2 cm to about 6 cm, is formed over the anterior side of the medial meniscus. Following retraction of the surrounding tissue, the anterior side of the medial meniscus is resected. A coarse rasp is then inserted between the medial condyle of the femur and medial condyle 21 of tibia 12. The rasp is used to remove approximately 1-2 mm of articular cartilage on medial facet 24 of tibia 12. Removal of the meniscus and the articular cartilage provides increased access to medial facet 24 of tibia 12.

Figure 2:
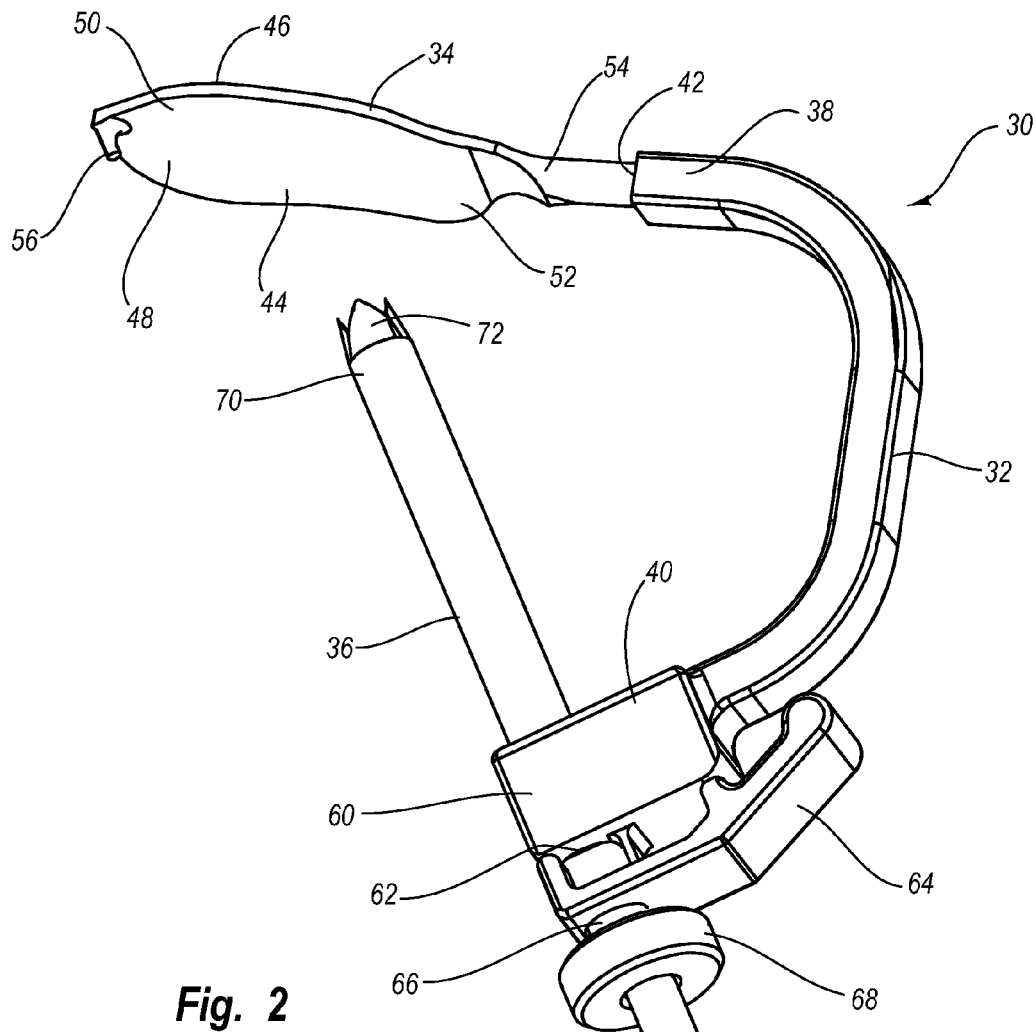
FIG. 2 is a perspective view of a guide assembly for forming a tunnel on the proximal end of the tibia shown in FIG. 1.

Depicted in FIG. 2 is one embodiment of a guide assembly 30 which is now used for forming a tunnel through a portion of tibia 12. As discussed below in greater detail, the tunnel can be used for preparing tibia 12 for a condylar implant and/or securing a condylar implant to tibia 12. In general, guide assembly 30 includes a substantially U-shaped guide brace 32 having a template 34 and a tubular guide sleeve 36 mounted on opposing ends thereof. More specifically, guide brace 32 has a first end 38 and an opposing second end 40. Recessed in first end 38 is a socket 42.

Template 34 comprises a low profile base plate 44 having a top surface 46 and an opposing bottom surface 48 which each extend between a first end 50 and an opposing second end 52. Although not required, in one embodiment bottom surface 48 has a configuration generally complementary to medial facet 24 of the superior auricular surface of tibia 12. Base plate 44 typically has a maximum thickness extending between surfaces 46 and 48 in a range between about 1 mm to about 4 mm. Projecting from second end 52 of base plate 44 is a stem 54. Stem 54 is configured to be slidably received within socket 42 of guide brace 32. A projection 56 downwardly extends from bottom surface 48 of base plate 44 at first end 50. As depicted, projection 56 has the configuration of a narrow finger. In other embodiments, projection 56 can comprise an elongated ridge or other configurations.

Formed on second end 40 of guide brace 32 is an enlarged housing 60 having a passage 62 extending therethrough. A resiliently flexible clamp arm 64 is mounted to housing 60. An aperture 66 extends through clamp arm 64 in general alignment with passage 62.

Tubular guide sleeve 36 slidably extends through passage 62 and aperture 66. Guide sleeve 36 has a proximal end 68 and an opposing distal end 70. A plurality of sharpened teeth 72 are formed at distal end 70. By pressing clamp arm 64 toward housing 60, passage 62 and aperture 66 are aligned allowing guide sleeve 36 to freely slide within passage 62 and aperture 66 to a desired location. As clamp arm 56 is released, clamp arm 56 resiliently biases away from housing 60 so as to bind guide sleeve 36, thereby securing guide sleeve 36 in the desired location. In alternative embodiments, it is appreciated that clamp arm 64 can be replaced with a set screw, clamp, or a variety of other types of fasteners that can be used to selectively secure guide sleeve 36 to second end 40 of guide brace 32.

Figure 3:
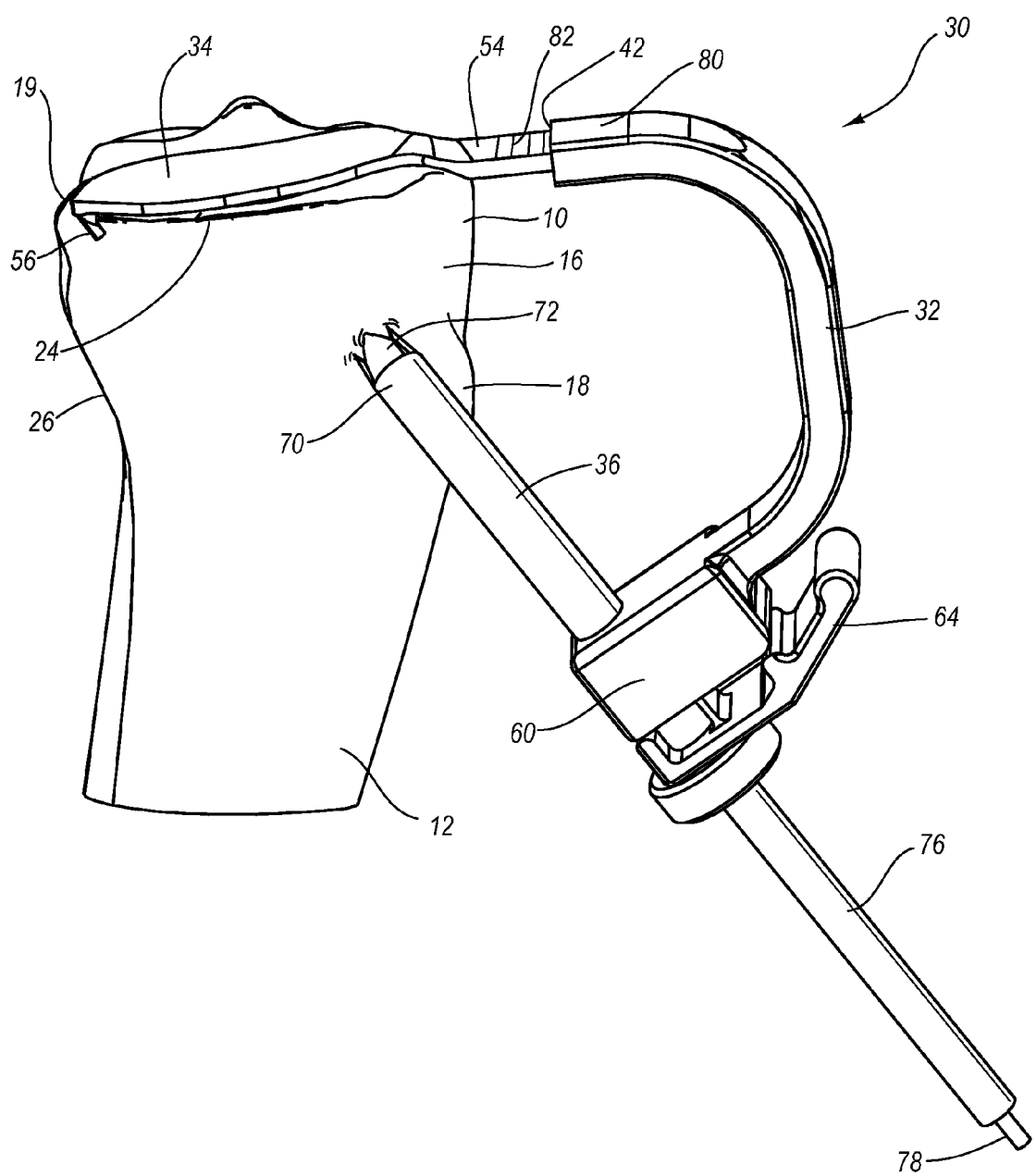
FIG. 3 is a perspective view showing the guide assembly in FIG. 2 mounted on the tibia of FIG. 1.

During use, as depicted in FIG. 3, template 34 is slid over medial facet 24 of tibia 12 so that projection finger 56 catches on posterior side 19 of tibia 12. Projection finger 56 thus facilitates proper positioning of template 34 and also, helps to retain template 34 on medial facet 24. It is appreciated that the size and shape of the lateral and medial facets of the superior articular surfaces of the tibia varies between different patients. As such, the present invention comprises a plurality of alternative templates 34 which are configured for placement on one of the lateral and medial facet and which each have a different configuration. As such a number of the alternative templates 34 can be initially test fitted to determine one that has a best fit for a particular patient.

Figure 2A:
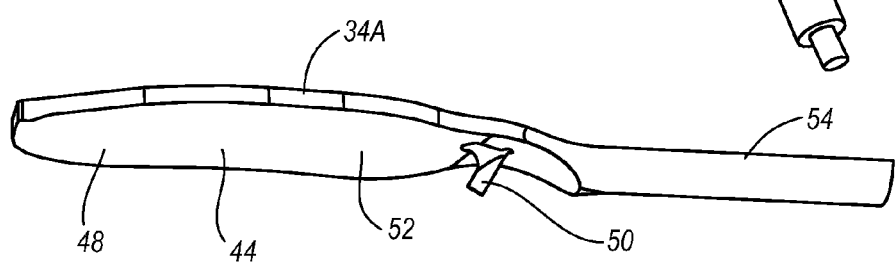
FIG. 2A is a perspective view of an alternative template used with the guide assembly shown in FIG. 2.

For example, depicted in FIG. 2A is one alternative template 34A that is smaller than template 34. Like elements between templates 34 and 34A are identified by like reference characters. In further contrast to template 34, template 34A has a projection 56A downwardly extending from second end 52 of base plate 44. Projection 56A thus biases against anterior side 18 or medial side 16 of tibia 12 to help properly position template 34A. In yet other embodiments, in contrast to positioning the projection on one of the opposing ends of base plate 44, the projection can be positioned along one of the opposing sides of base plate 44 so as to bias against lateral side 14 (when used on lateral facet 22) or bias against medial side 16 of tibia 12.

Once template 34 is selected and properly positioned on medial facet 24, tubular guide sleeve 36 is advanced within housing 60 so that teeth 72 at distal end 70 bias against medial side 16 of proximal end 10 of tibia 12. Guide sleeve 36 is then secured in place by releasing clamp arm 64. By securing guide sleeve 36 against tibia 12, guide assembly 30 is clamped onto tibia 12. In one alternative embodiment, guide sleeve 36 can be biased against anterior side 18 of tibia 12.

Next, a tubular drill sleeve 76 is inserted into tubular guide sleeve 60. Positioned within drill sleeve 76 is a guide wire 78. Using drill sleeve 76 as a guide, guide wire 78 is drilled through tibia 12 until guide wire 78 reaches template 34, thereby forming a guide tunnel. In part, template 34 functions as a shield to prevent guide wire 78 and/or other drill tools from accidentally contacting and damaging the femur. In other embodiments, a hole or recess is formed on template 34. Guide wire 78 can passed through or into the hole or recess to ensure complete formation of the tunnel on medial facet 24.

Once the guide tunnel is formed, guide wire 78 and drill sleeve 76 are removed from guide sleeve 60. A larger drill tool, not show, such as a larger guide wire, drill bit, or the like is then passed through guide sleeve 60 and drilled through tibia 12 along the guide tunnel to form a final tunnel 90 (FIG. 4) through tibia 12. It is appreciated that any number of progressively larger drill tools can be used. In alternative embodiments guide wire 78 and drill sleeve 76 can be eliminated. A single larger drill tool can then be used to form tunnel 90 in a single pass. Using a sequence of larger drill tools, however, helps ensure proper placement of tunnel 90 and facilitates forming the opening of the tunnel adjacent to template 34.

As discussed below in greater detail, the angular orientation of tunnel 90 is typically held constant and is based on the configuration of the implant. However, depending on the amount of bone needed to be resected for mounting the condylar implant, it may be necessary to shift the position of tunnel 90 posterior or anterior. Shifting the position of tunnel 90 posterior-anterior is accomplished by selectively moving stem 54 of template 34 further into or further out of socket 42 of guide brace 32. Once template 34 and guide brace 32 are positioned at their relative positions, a set screw 80 is tightened so as to secure template 34 and guide brace 32 together. Predefined markings 82 are formed on stem 54 to help define the relative positioning between template 34 and guide brace 32.

Figure 4:
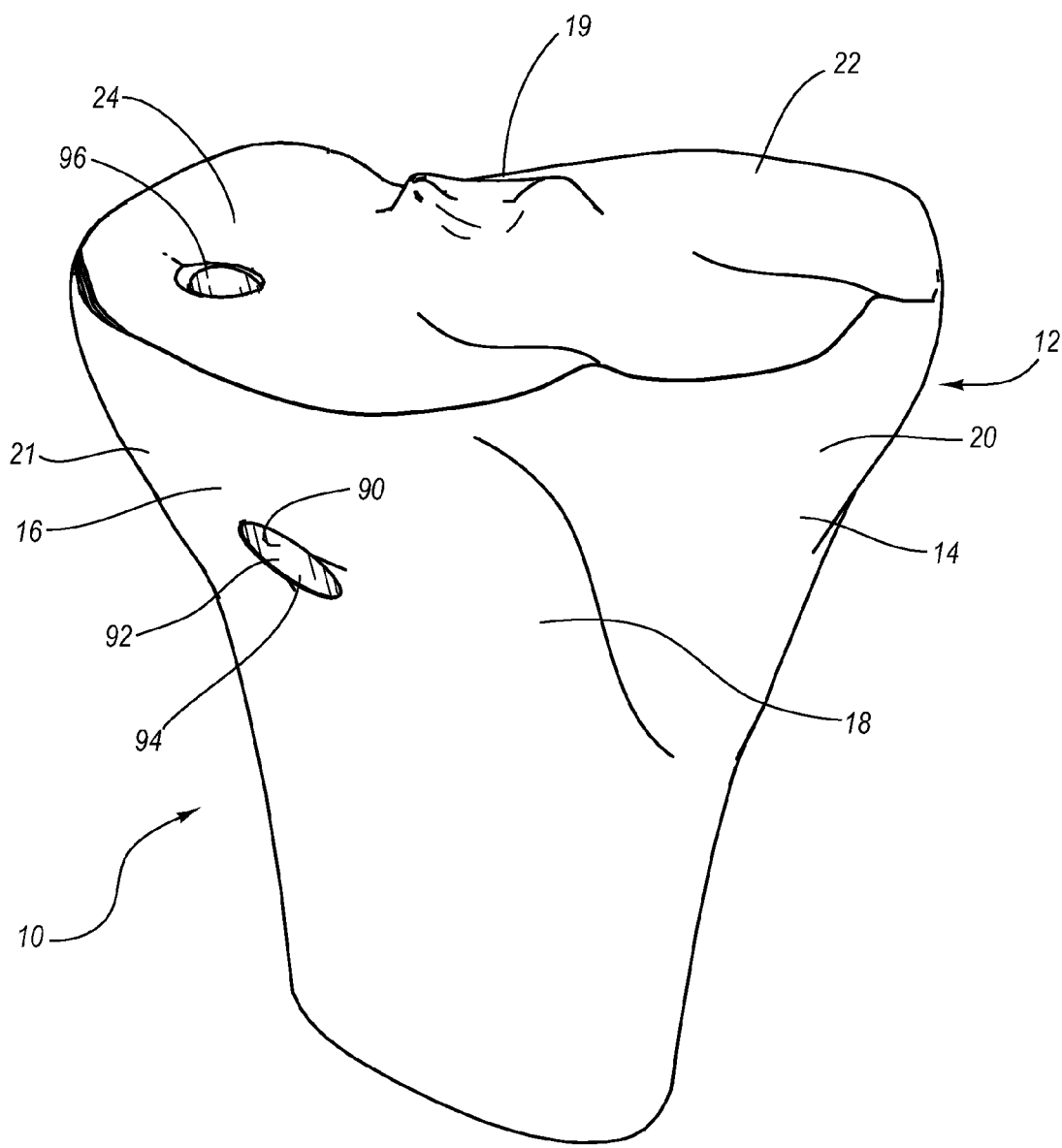
FIG. 4 is a perspective view of the tibia shown in FIG. 1 having a tunnel formed thereon.

Once tunnel 90 is formed, guide assembly 30 is removed so as to produce tibia 12 shown in FIG. 4. As depicted, tunnel 90 has an interior surface 92 that extends from a proximal end 94 to an opposing end distal end 96. Proximal end 94 is formed on medial side 16 of proximal end 10 of tibia 12. Distal end 96 is formed on medial facet 24 of tibia 12. Although tunnel 90 can be any desired size, in one embodiment tunnel 90 has a diameter in a range between about 5 mm to about 10 mm.

Using the above discussed methods and instruments, tunnel 90 is formed by procedures that are minimally invasive to the patient. As discussed below in greater detail, once tunnel 90 is formed, tunnel 90 can then be used to assist in the resection of medial fact 24 and/or the mounting of a condylar implant on the resected medial facet 24. Furthermore, by using tunnel 90 the resection of medial facet 24 and the mounting of the condylar implant can also be performed using procedures that are minimally invasive.

Figure 5:
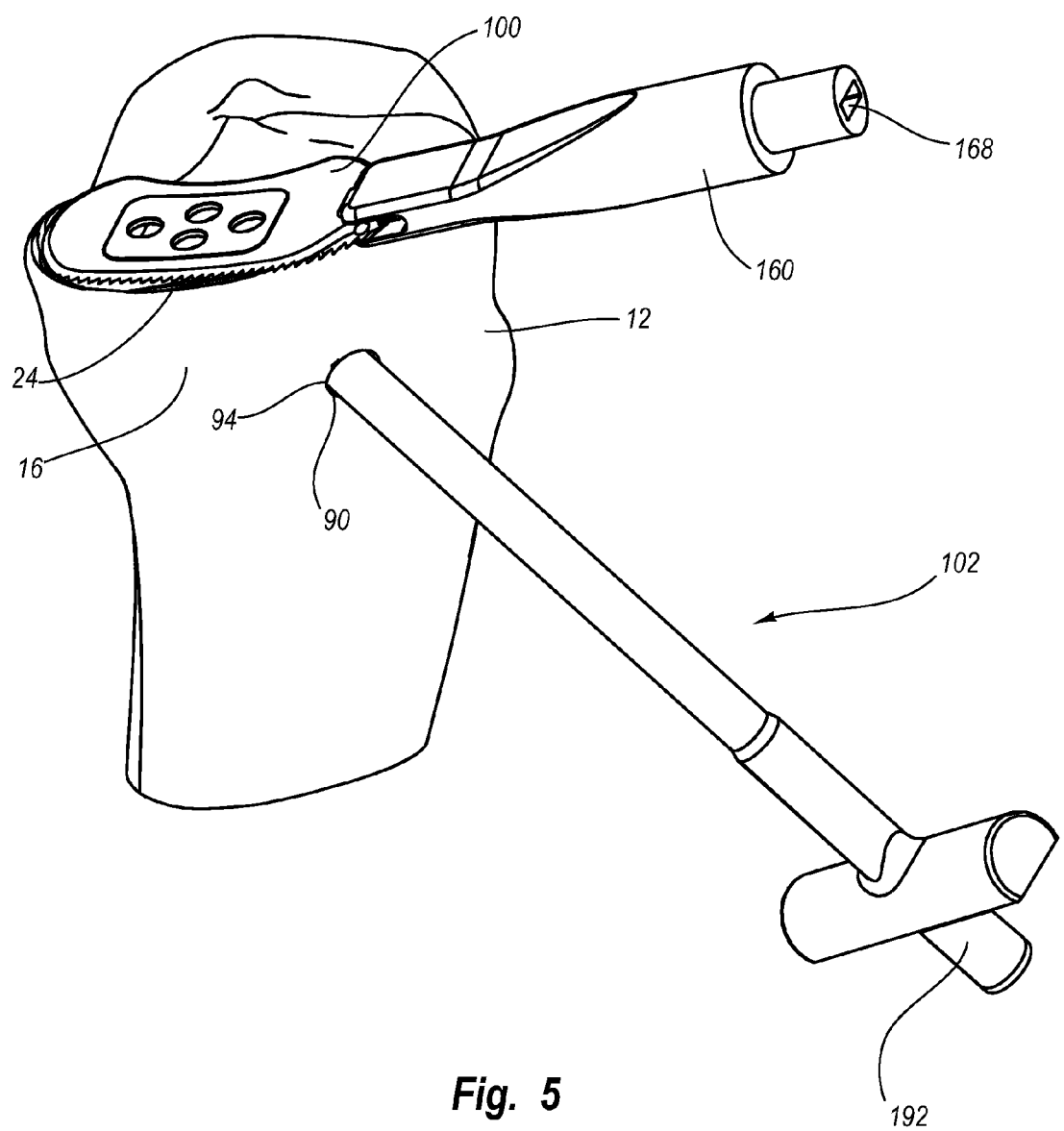
FIG. 5 is a perspective view of a rasp assembly resecting the tibia of FIG. 4.

Although not required, in one embodiment as mentioned above tunnel 90 is used in the resection of tibia 12 for preparing tibia 12 to receive a condylar implant. The resection of tibia 12 can be accomplished using a number of different procedures. For example, as depicted in FIG. 5, is one embodiment of a rasp assembly 100 is used in association with a retention rod 102 to facilitate resection of tibia 12.

Figure 6:
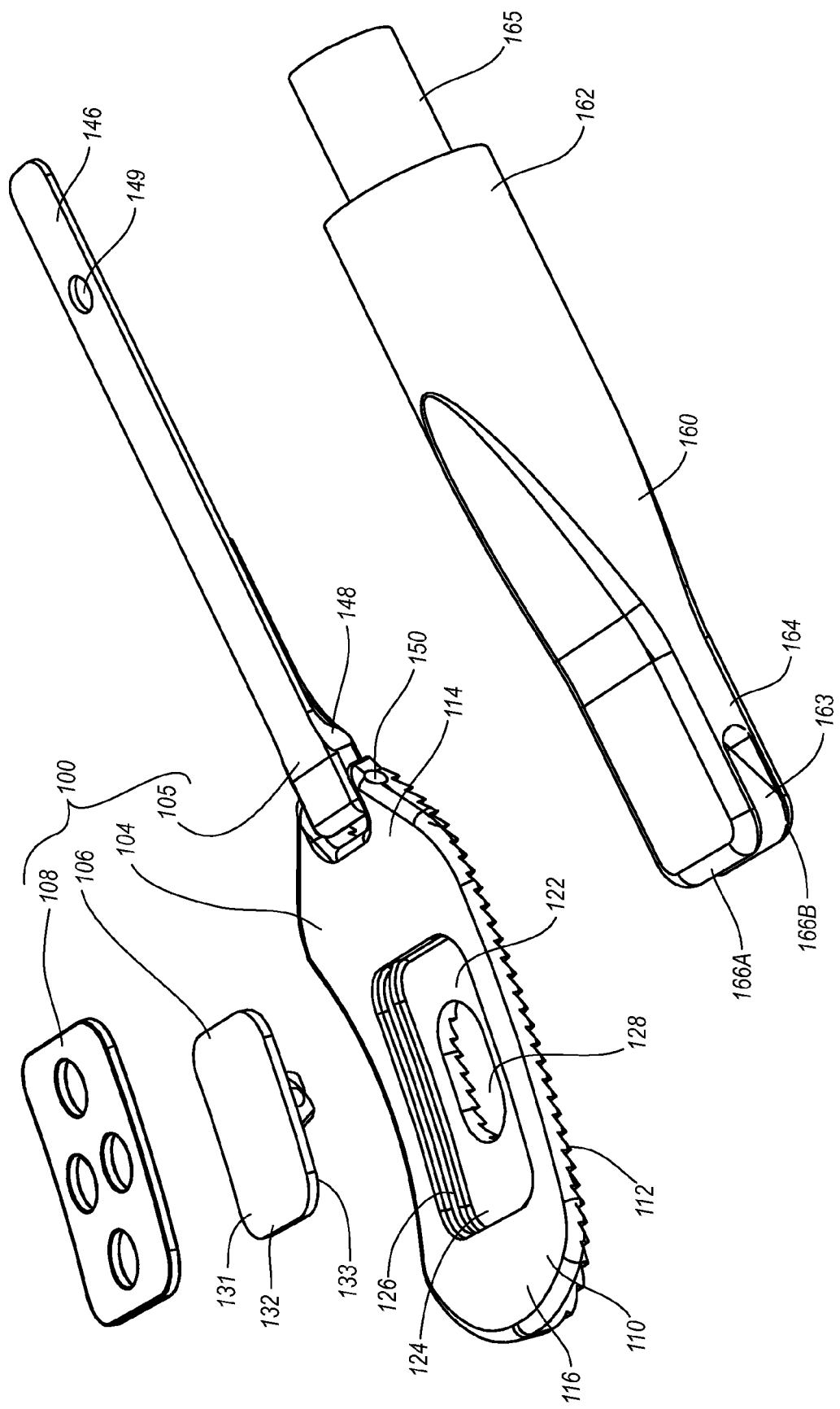
FIG. 6 is a top perspective view of the raps assembly shown in FIG. 5.
Figure 7:
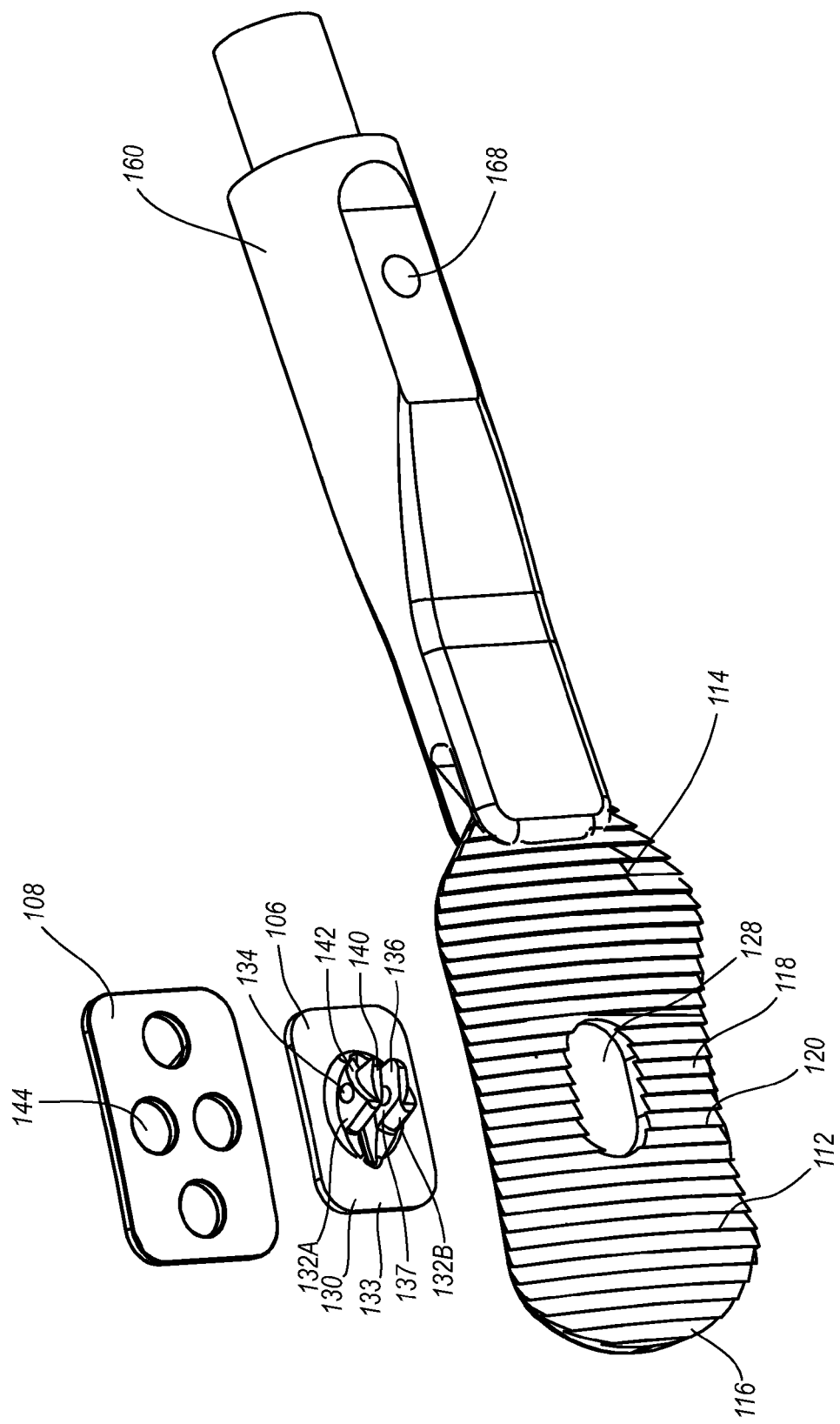
FIG. 7 is a bottom perspective view of the rasp assembly shown in FIG. 6.

As depicted in FIG. 6, rasp assembly 100 comprises a rasp body 104 having a pivot arm 105 mounted thereon, a rasp guide 106, and a cover plate 108. More specifically, as depicted in FIGS. 6 and 7, rasp body 104 has a top surface 110 and an opposing bottom surface 112 that each extend between a proximal end 114 and an opposing distal end 116. Transversely extending across bottom surface 112 are a plurality of ridges 118 that each terminate at a sharpened cutting edge 120. It is appreciated that ridges 188 and cutting edges 120 can be at any desired orientation or combination of different orientation that facilitate cutting. Bottom surface 112 is configured such that reciprocating movement of bottom surface 112 on tibia 12 produces a recess on tibia 12 that can receive a desired implant. Recessed on top surface 110 of rasp body 104 is a guide slot 122. Guide slot 122 is bounded by a floor 124 and a sidewall 126 upstanding from floor 124. Extending through floor 124 to bottom surface 112 is an opening 128.

Rasp guide 106 comprises a slide plate 130 having a top surface 131 and an opposing bottom surface 133. Downwardly projecting from bottom surface 133 are a pair of spaced apart forks 132A and 132B with a pin 134 extending therebetween. Forks 132A and B have facing interior surfaces 136 which bound a gap 137 and have opposing exterior surfaces 138. Forks 132A and B terminate at a free terminus 140. Exterior surface 138 of each fork 132A and B is recessed at terminus 140 such that a sloping shoulder 142 is formed on each fork 132A and B.

Rasp guide 106 is received within guide slot 122 so that forks 132A and B project through opening 128. Rasp guide 106 is slightly smaller than guide slot 122 such that forks 132A and B are free to reciprocate within opening 128 as slide plate 130 reciprocates within guide slot 122. As shown in FIG. 5, cover plate 108 is secured within guide slot 122 so as to retain rasp guide 106 within guide slot 122. Cover plate 108 can be mounted using conventional techniques such as welding, press fit, and the like. Holes 144 are formed through cover plate 108 to prevent unwanted build-up of resected bone particles within guide slot 122.

As depicted in FIG. 6, pivot arm 105 has a proximal end 146 and an opposing distal end 148. A set hole 149 extends through pivot arm 105 toward proximal end 146. Distal end 148 of arm 105 is hingedly mounted to proximal end 114 of rasp body 104 by a pin 150.

In one embodiment, an insertion handle 160 is used to place rasp body 104 over medial facet 24 of tibia 12. Insertion handle 160 has a proximal end 162 and an opposing distal end 164. A post 165 is formed a proximal end 162. Post 165 is adapted to receive an extension handle if desired. A pair of spaced apart lips 166A and B project from distal end 164 and bound a slot 163. A channel 168 (FIG. 5) longitudinally extends through insertion handle 160 so as to communicate with slot 163. Channel 168 is configured to receive pivot arm 105 when rasp body 104 is received within slot 163.

During use, pivot arm 105 is slid into channel 165 from between lips 166A and B. Lips 166A and B are then advanced to extend above and below proximal end 114 of rasp body 104. A set screw 168 (FIG. 7) is then advanced into insertion handle 160 so as to extend through set hole 149 on pivot arm 105. In this configuration insertion handle 160 rigidly supports rasp body 104 so as to prevent hinged movement of rasp body 104 during insertion.

Figure 8:
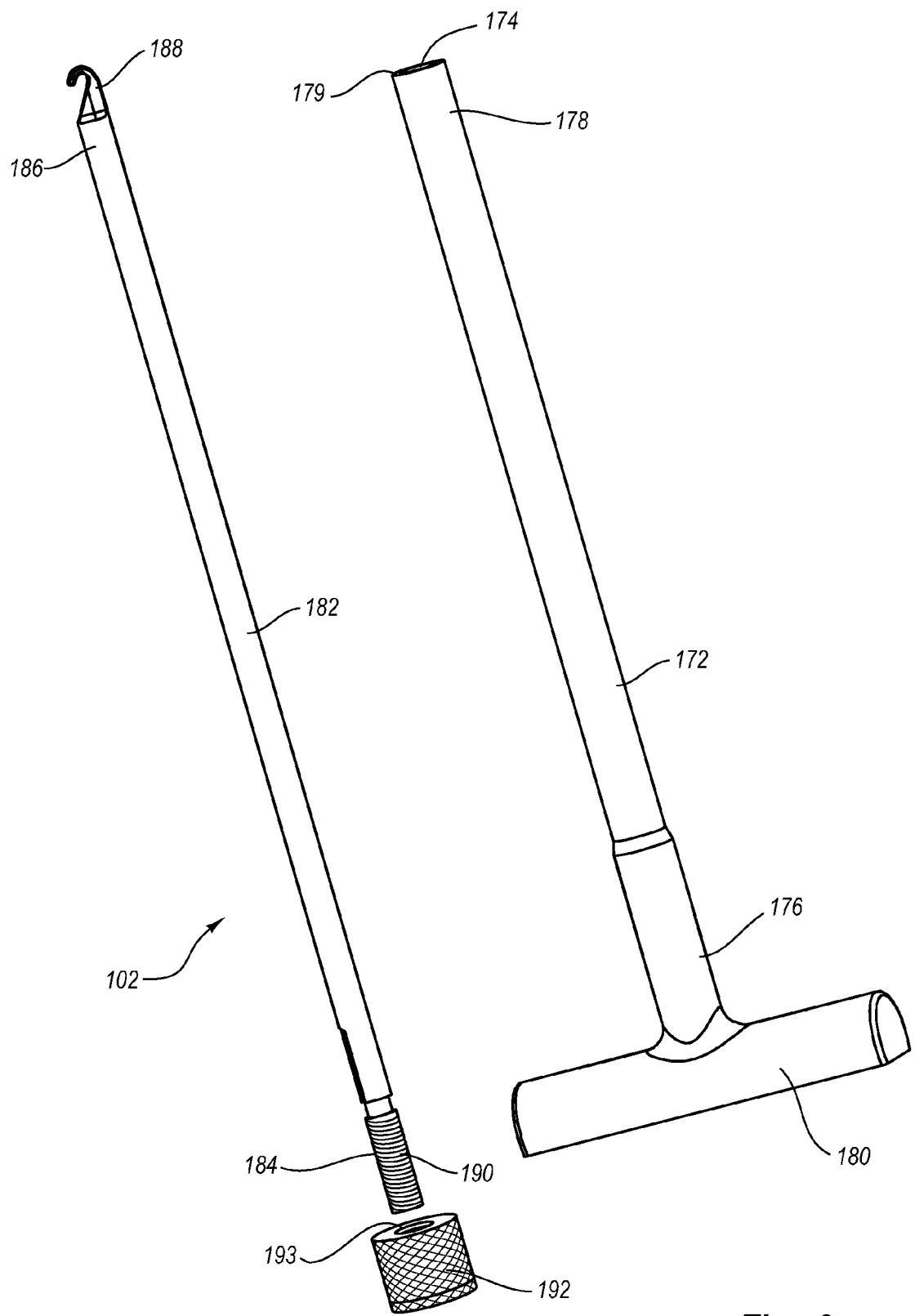
FIG. 8 is an exploded perspective view of the retention rod shown in FIG. 5.

Turning to FIG. 8, retention rod 102 comprises a tubular set rod 172 bounding a channel 174 extending from a proximal end 176 to an opposing distal end 178. Distal end 178 terminates at a distal end face 179. A handle 180 outwardly projects from proximal end 176 to facilitating grasping retention rod 102.

Retention rod 102 further comprises a hook rod 182. Hook rod 182 has a proximal end 184 and an opposing distal end 186. Projecting from distal end 186 is a hook 188. Threads 190 are formed on proximal end 184. A knob 192 is also provided having a threaded port 193. Threads 190 on hook rod 182 are configured to mate with threaded port 193 of knob 192. Hook rod 182 is received within channel 174 of set rod 172 such that knob 192 biases against handle 180 and hook 188 extends beyond distal end face 179. In this configuration, rotation of knob 192 relative to hook rod 182 causes hook 188 to extend or retract relative to set rod 172.

Figure 9A:
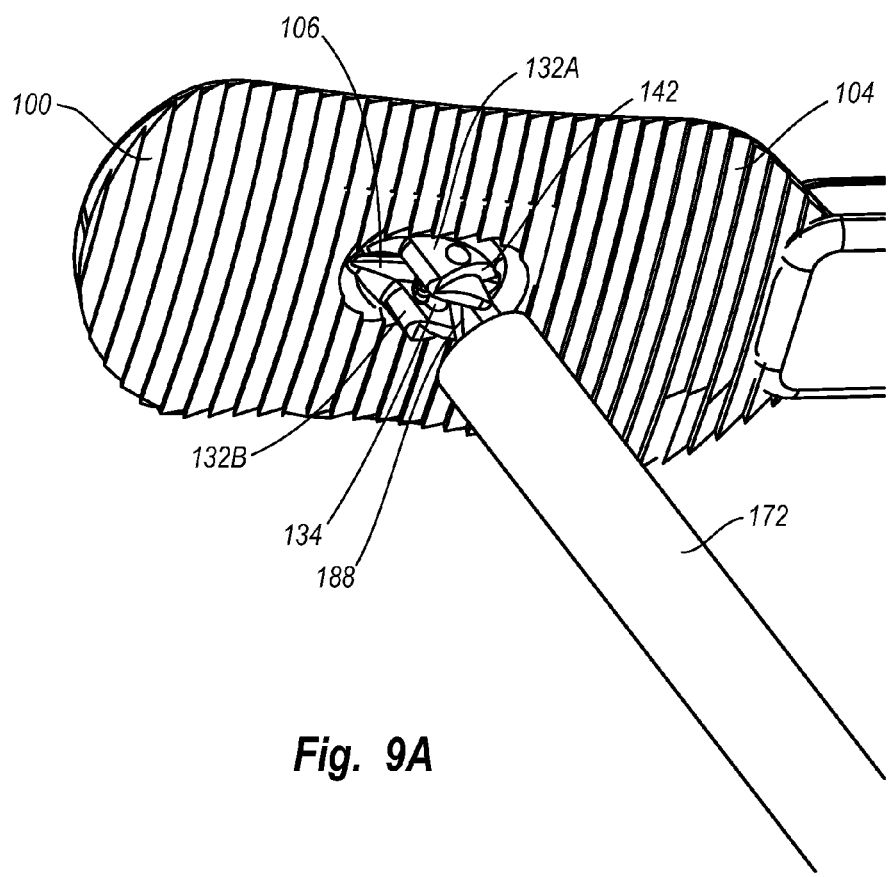
FIGS. 9A and 9B are perspective views of the retention rod shown in FIG. 8 being mounted to the rasp assembly shown in FIG. 5.

During operation, as depicted in FIG. 5, rasp assembly 100 is mounted on medial facet 24 of tibia 12. Rasp assembly 100 is positioned using the rigidly mounted insertion handle 160, as discussed above, such that forks 132A and B (FIG. 7) are aligned with the distal end of tunnel 90. Once rasp assembly 100 is positioned, retention rod 102 is advance within tunnel 90 from proximal end 94. As depicted in FIG. 9A, knob 192 is rotated so that hook 188 extends beyond set rod 172. With hook 188 freely exposed, hook 188 is hooked over pin 134 extending between forks 132A and B.

Figure 9B:
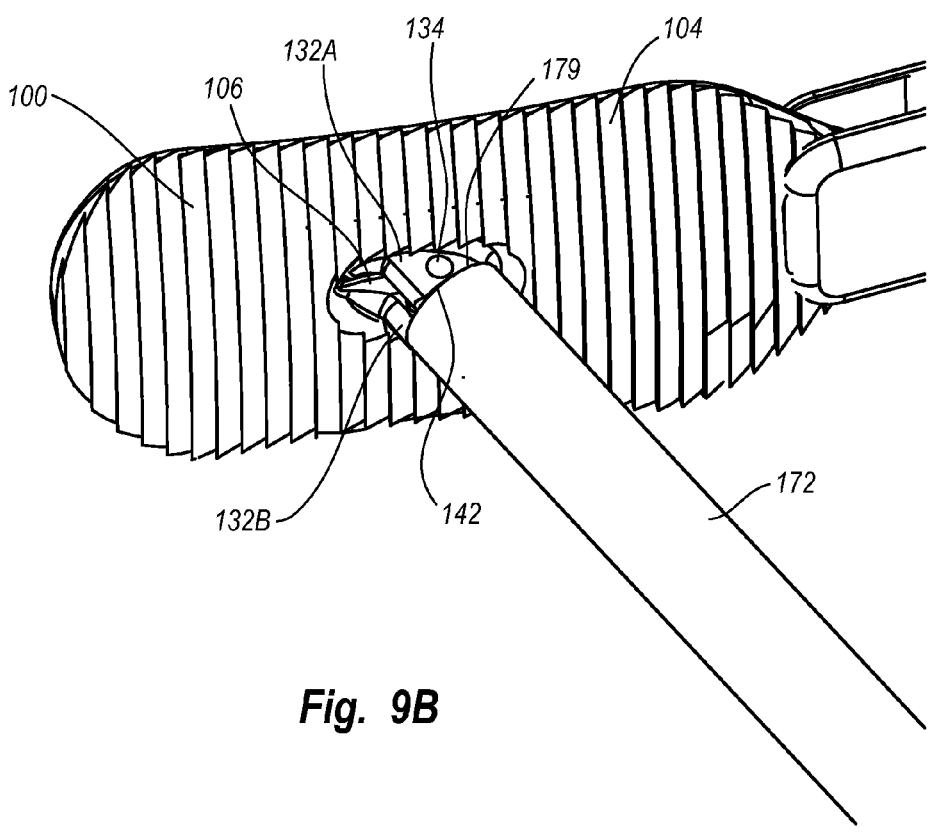

As depicted in FIG. 9B, once hook 188 has captured pin 134, knob 192 is rotated so as to advance set rod 172 toward hook 188. Set rod 172 is advanced until distal end face 179 of set rod 172 biases against shoulders 142 of forks 132A and B. Shoulders 142 are sloped such that end face 179 can sit flush against shoulder 142 while set rod 172 retains its orientation within tunnel 90. In this configuration, retention rod 102 is securely fixed to rasp guide 106.

Once retention rod 102 is secured to rasp assembly 100, insertion handle 160 is removed from pivot arm 105. A reciprocal driver, such as a reciprocal saw, not shown, is then connected pivot arm 105. While holding rasp guide 106 substantially stationary by holding onto retention rod 102, the reciprocal driver rapidly reciprocates rasp body 104 so that cutting edges 120 resect medial facet 24 of tibia 12. In one embodiment, rasp body 104 reciprocates along a length in a range between about 1 mm to about 4 mm. Other dimensions can also be used.

In one embodiment bottom surface 112 of rasp body 104 slightly arched. By having pivot arm 105 hingedly attached to rasp body 104, rasp body 104 is free to reciprocate along the arched path. The hinged attachment also helps to minimize binding of rasp body 104. In alternative embodiments, arm 105 can be rigidly attached to rasp body 104.

In one embodiment of the present invention means are provided for removably engaging retention rod 102 with rasp body 104 such that rasp body 104 can be selectively reciprocated without substantial movement of retention rod 102. By way of example and not by limitation, one embodiment of the means comprises rasp guide 106 slidably mounted on rasp body 104 and hook 188 mounted on retention rod 102. In alternative embodiments it is appreciated that a variety of different structures can accomplish the same function. For example, pin 134 and hook 188 can be replaced with a threaded connection, bayonet connection, or any number of other conventional connections which allows retention rod 102 to engage with rasp guide 106.

It is also appreciated that rasp guide 106 can be mounted on rasp body 104 in a variety of different ways. For example, opening 128 can extend through rasp body 104 without the formation of guide slot 122. In this embodiment slide plate 130 can be positioned directly on top surface 110 of rasp body 104 while forks 132A and B extend through opening 128. In yet another alternative, guide slot 122 can be formed on bottom surface 112 of rasp body 104. Cover plate 108 can be formed having opening 128 extending therethrough and cutting edges 120 formed on a bottom surface thereof. Slide plate 130 can be positioned within the guide slot 122 so that when cover plate 108 is secured over guide slot 122, forks 132A and B extend through opening 128 formed on cover plate 108.

It is also appreciated that retention rod 102 can have a variety of different configurations. For example, in alternative embodiments set rod 172 can be eliminated. As such, retention rod 102 can simply comprise hook rod 182. Furthermore, as discussed above, hook 188 can be replaced with a variety of different types of connectors.

Figure 10:
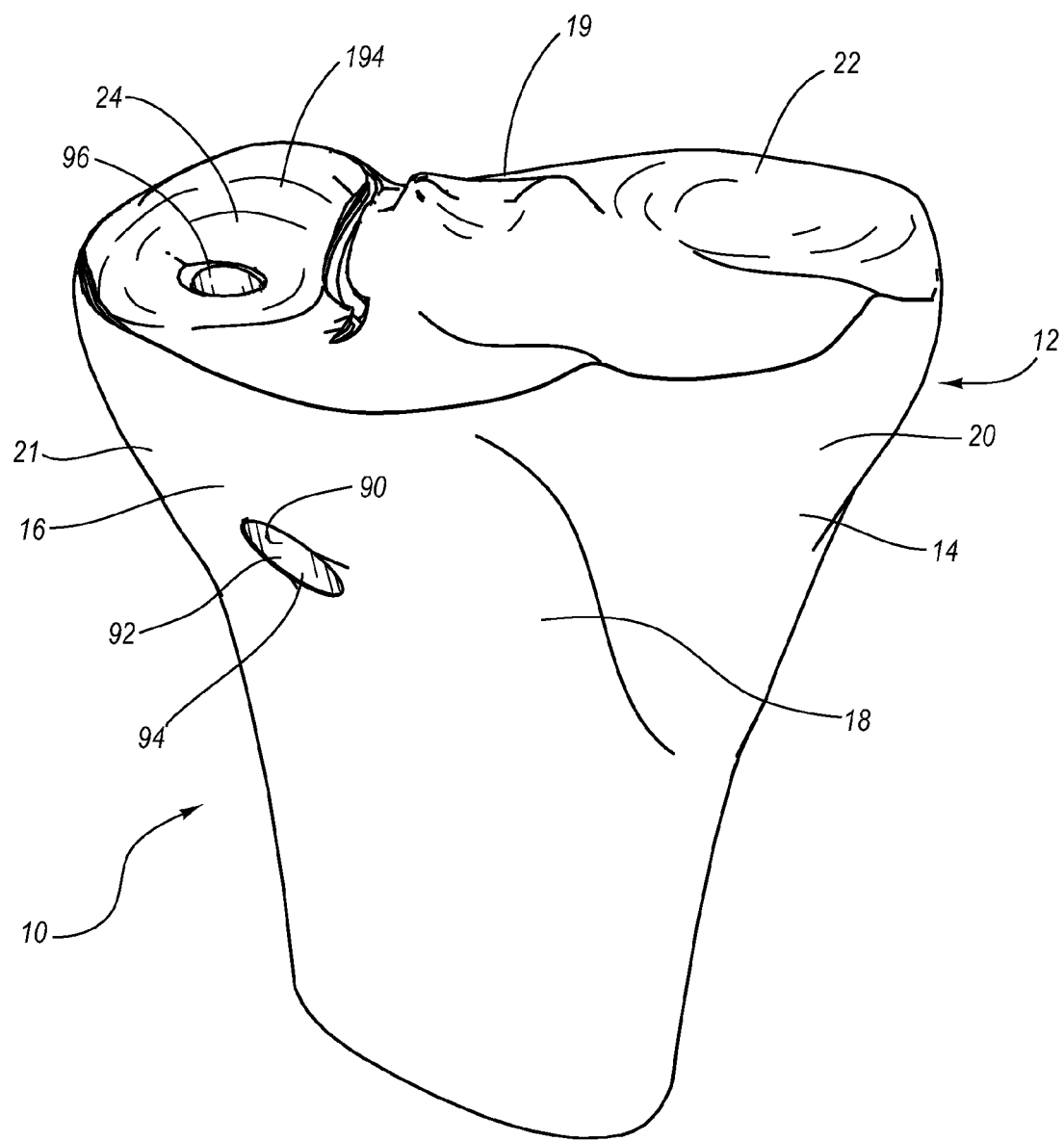
FIG. 10 is a perspective view of the tibia shown in FIG. 4 having a recess formed thereon.

Once medial facet 24 has been sufficiently resected by rasp body 104, rasp assembly 100 and retention rod 102 are removed. The resected bone particles are removed by conventional flushing and suction. As depicted in FIG. 10, tibia 12 now has a resected recess 194 formed on medial facet 24.

Figure 11:
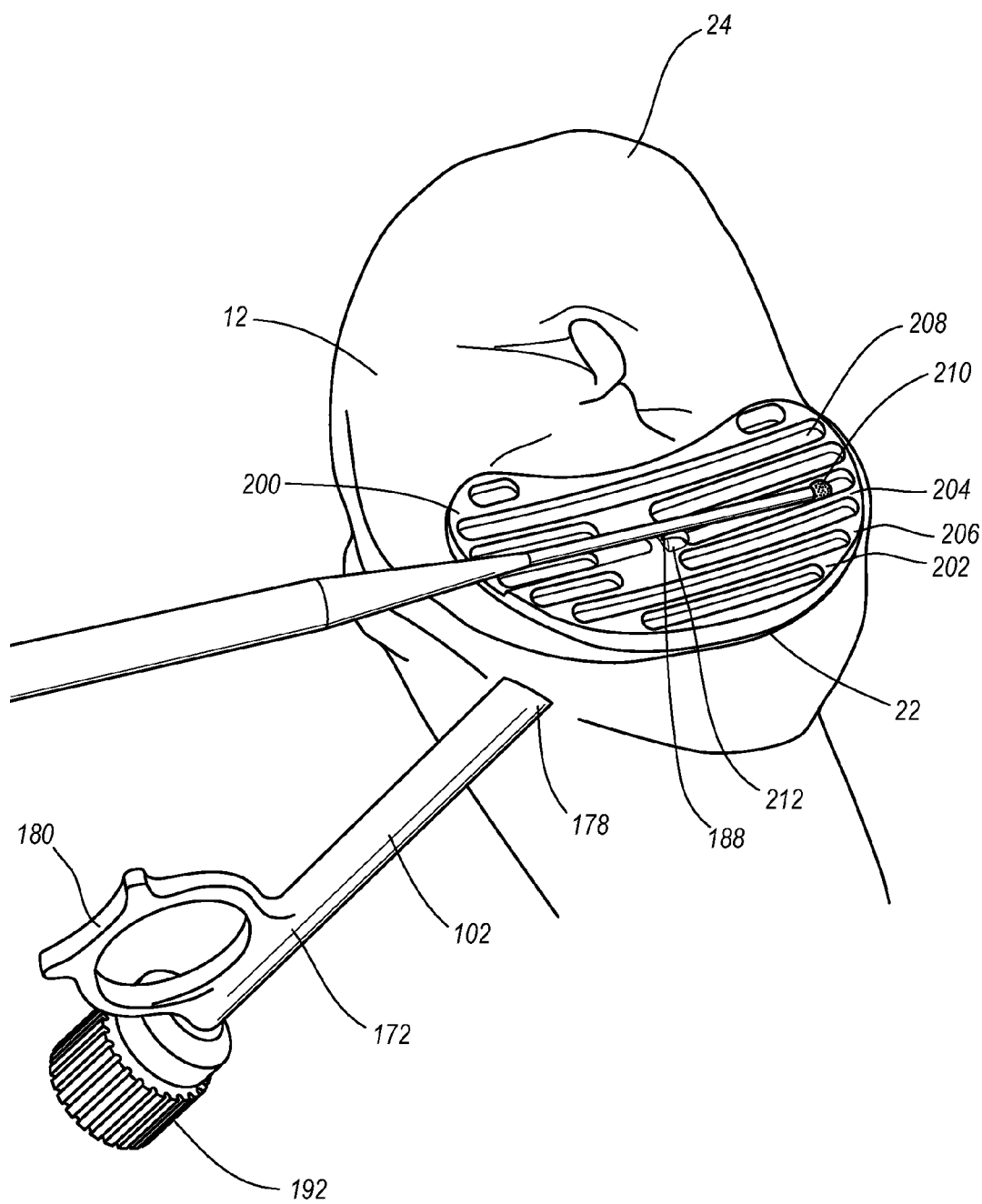
FIG. 11 is a perspective view of a cutting template being mounted on the tibia shown in FIG. 4.

It is appreciated that the resection of tibia 12 can be accomplished using a variety of different techniques. For example, in one alternative depicted in FIG. 11, the resection of tibia 12 is accomplished by cutting through an area bounded by a cutting template 200. Cutting template 200 comprises a plate 202 having a top surface 204 and an opposing bottom surface 206. In the embodiment depicted cutting template 200 is configured to rest on lateral facet 22 of tibia 12. Of course, cutting template 200 can also be designed for resting on medial facet 24.

Extending between opposing surfaces 204 and 206 are a plurality of guide spaces 208. Guide spaces 208 are formed so that when cutting template 200 is positioned, guide spaces 208 are positioned over at least a portion of the facet to be resected. In the embodiment depicted, guide spaces 208 have the configuration of an elongated channel. As will be discussed below in greater detail, the channels facilitate guided receipt of a cutting burr 210 which is used to selectively remove the unwanted bone. In alternative embodiments, depending on the type and size of tool used to remove the bone, guide spaces 208 can come in a variety of different sizes, shapes, and orientations.

In one embodiment, although not required or shown, a second cutting template is provided having guide spaces extending therethrough. In the second cutting template, the guide spaces are aligned so as to bound the area of the facet to be resected which was blocked by plate 202 of cutting template 200. As a result, by sequentially using both cutting templates, all or at least a greater proportion of the bone can be removed by cutting burr 210. Additional cutting templates can also be used.

Cutting template 200 is used in association with retention rod 102 as previously discussed. In the embodiment depicted, handle 180 has a different configuration. During use, cutting template 200 is position over lateral facet 22. Distal end 178 of set rod 172 is advanced through tunnel 90 so that hook 188 of hook rod 182 projects out of set rod 172. Hook 188 is passed though a guide space 208 and then pulled back onto top surface 204 of plate 202. A rib 212 upwardly projects from plate 202 adjacent to guide space 208. Hook 188 is hooked over rib 212 so as to improve the engagement between hook 188 and cutting template 200.

Once hook 188 is engaged to cutting template 200, knob 192 is rotated so as to bias set rod 172 against bottom surface 206 of template 200. As a result, retention rod 102 is securely clamped to cutting template 200. Accordingly, by pulling retention rod 102, cutting template 200 is securely held in place on lateral facet 22. Cutting burr 210 or some other form of drill bit is then advanced into and along each of guide spaces 208 so as to resect the portion of the bone directly below guide space 208. As previously discussed, in one embodiment cutting template 200 can be removed and replaced with a second template. Burr 100 can then be passed through guide spaces of the second template to remove further bone that was covered by cutting template 200.

In other alternatives, it is appreciated that once cutting template 200 is removed, the remaining bone portion can be removed by sight and feel without the use of a template. In yet other embodiments, depending on the type and amount of bone needed to be resected, a single template can be rotated or shifted on lateral facet 22 so that the single template is used to remove the desired bone.

In one embodiment of the present invention, means are provided for removably engaging retention rod 102 to cutting template 200 so that retention rod 102 secures cutting template 200 to the lateral or medial facet of tibia 12 when retention rod 102 is received within tunnel 90 of tibia 12. By way of example and not by limitation, one embodiment of such means comprises hook 188 and guide space 208 which enables hook 188 to engage with cutting template 200.

The present invention also envisions that there are a variety of other structures that can accomplish the same function. For example, the same structures and techniques as discussed above for securing retention rod 102 to rasp assembly 100 can also be used with cutting template 200. That is, in one alternative forks 132A and B with pin 134 can be mounted on bottom surface 206 of plate 202. Other connections such as threaded connection, bayonet connections, and the like can also be used.

By using the above discussed instruments and methods, the lateral and medial facets of tibia 12 can be selectively resected by procedures that are minimally invasive.

Figure 12A:
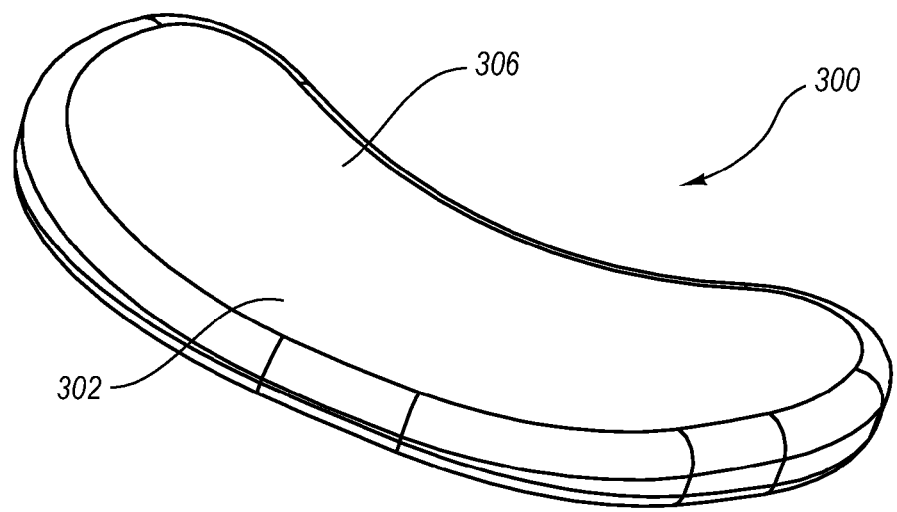
FIG. 12A is a top perspective view of a condylar implant.
Figure 12B:
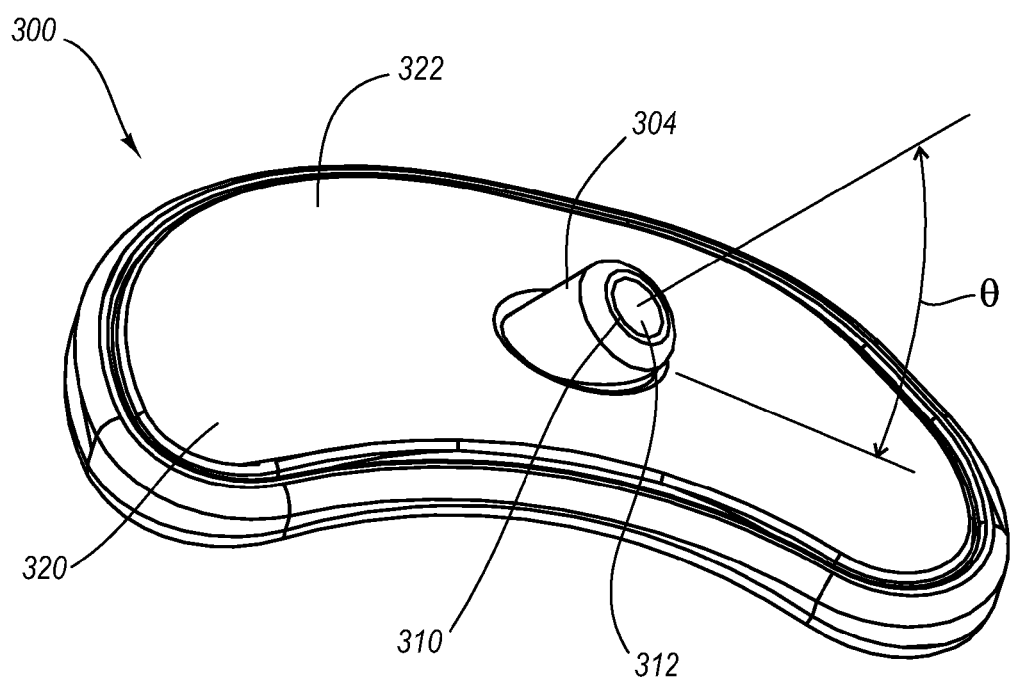
FIG. 12B is a bottom perspective view of the condylar implant shown in FIG. 12A.
Figure 12C:
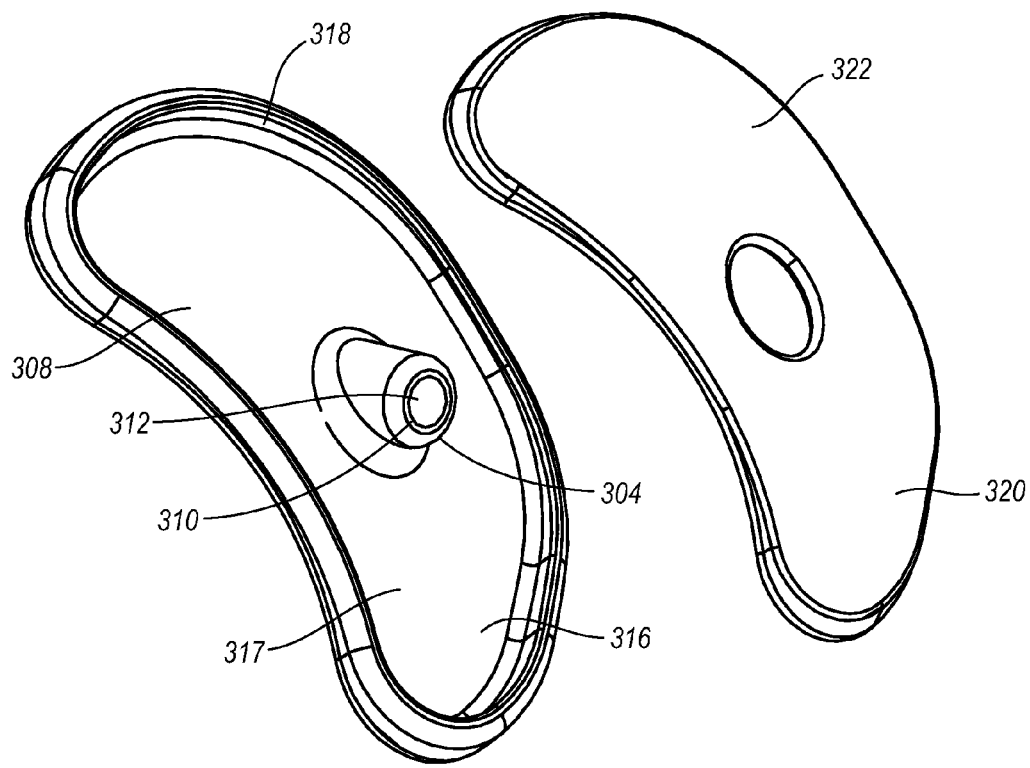
FIG. 12C is an exploded perspective view of the condylar implant shown in FIG. 12B.

Depicted in FIGS. 12A-12C is one embodiment of a condylar implant 300 incorporating features of the present invention. The term "condylar implant" is broadly intended to include implants that can replace all or a portion of a condyle of a tibia. Accordingly, while the depicted embodiments show one conventional size and configuration for a condylar implant, in alternative embodiments the condylar implant can be larger to replace more of the tibia or can be smaller to replace only a section of a condyle of a tibia. In such alternatives, the condylar implant can have a variety of different configurations.

Condylar implant 300 comprises a bearing plate 302 having a stem 304 projecting therefrom and an inlay 320. More specifically, bearing plate 302 comprises a top articular surface 306 and an opposing bottom surface 308. In one embodiment, top articular surface 306 is contoured to mate with a corresponding femoral condyle.

A pocket 316 is recess on bottom surface 308. Pocket 316 is bounded by a floor 317 and a sidewall 318 upstanding around the perimeter thereof. Stem 304 projects from bottom surface 308 and terminates at a distal terminus 310. Recessed within distal terminus is a threaded socket 312. Bearing plate 302 and stem 304 are typically comprised of a metal such as chromium, cobalt, titanium, or the like and alloys thereof but can also be made of ceramics or plastics. Bearing plate 302 and/or stem 304 can also be comprised of layers or sections of different materials. In one embodiment, bearing plate 302 has a maximum thickness typically in a range between about 2 mm to about 10 mm. Other dimensions can also be used depending on the amount that the tibial condyle is resected or worn away.

In one embodiment of the present invention, means are provided for connecting a fastener to stem 304. One example of such means comprises threaded socket 312 as discussed above. In alternative embodiments, the threads within the socket on stem 304 could be replaced with bayonet slots, bayonet posts, ribs which are configured to mate with barbs or other forms of connectors. The socket can also be filled with an adhesive. In still other embodiments, the socket can be eliminated and threads, bayonet posts, barbs or other forms of connections can be formed on the exterior of stem 304.

Secured within pocket 316 so as to encircle stem 304 is inlay 320. Inlay 320 is comprised of a porous bone ingrowth material such as porous tantalum. Other conventional porous bone ingrowth materials can also be used. Inlay 320 is secured within pocket 316 using conventional techniques such as press fit, welding, adhesive, and the like. Inlay 322 has an exposed bottom surface 322 that can be substantially flat, arched, or can have any other desired configuration.

Centrally extending through stem 304 is a central longitudinal axis 314. In one embodiment, stem 304 projects from floor 317 so as to form an angle θ between central longitudinal axis 314 and inlay 320 in a range between about 30° to about 60°. Other angles can also be used. Stem 304 typically has a length in a range between about 2 mm to about 10 mm. Other dimensions can also be used.

It is appreciated that condylar implant 300 can have a variety of alternative configurations. For example, stem 304 is primarily formed to provide sufficient room for socket 312 when bearing plate 302 has a relative small thickness. As the thickness of bearing plate 302 increases, stem 304 can be increasingly shortened as more of socket 312 can be formed directly into bearing plate 302. As such, in some embodiments stem 304 can be eliminated in that all of socket 312 can be formed directly on bearing plate 302.

Furthermore, in the depicted condylar implant 300, pocket 316 is formed to receive inlay 320. In alternative embodiments pocket 316 can be eliminated and a section of the porous bone ingrowth material can be mounted on the bottom surface of bearing plate 302 using other conventional fastening techniques such as adhesives, screws, alternative press fits, and the like. Furthermore, in contrast to one pocket 316, a it plurality of spaced apart pockets can be formed on bottom surface 308 with each pocket receiving a separate inlay 320. Here it is noted that spikes, fins, or other forms of projections can also be formed projecting from bottom surface 308 of bearing plate 302. These projections can penetrate into the tibia or be received within slots formed on the tibia to help prevent movement of bearing plate 302.

Figure 13:
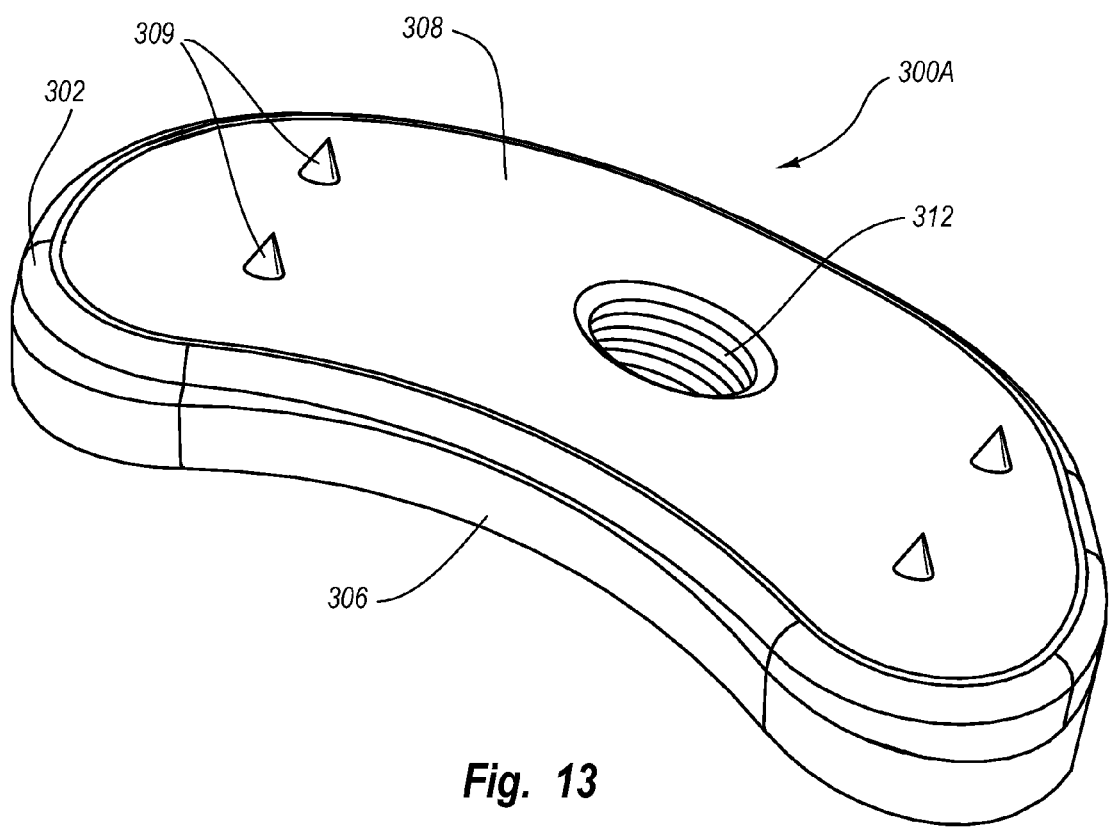
FIG. 13 is a perspective view of an alternative embodiment of a condylar implant.

In still other embodiments, it is appreciated that inlay 320 or other forms of the porous bone ingrowth material can be eliminated. In this embodiment, the condylar implant can comprise a single integral or monolithic member. For example, depicted in FIG. 13 is an alternative embodiment of a condylar implant 300A. Implant 300A is formed as a single integral member having top surface 306 and bottom surface 308. Because of the increased thickness of implant 300A, stem 304 is eliminated. Threaded socket 312 is formed directly on bottom surface 308. Projections 309 extend from bottom surface 308.

Figure 14:
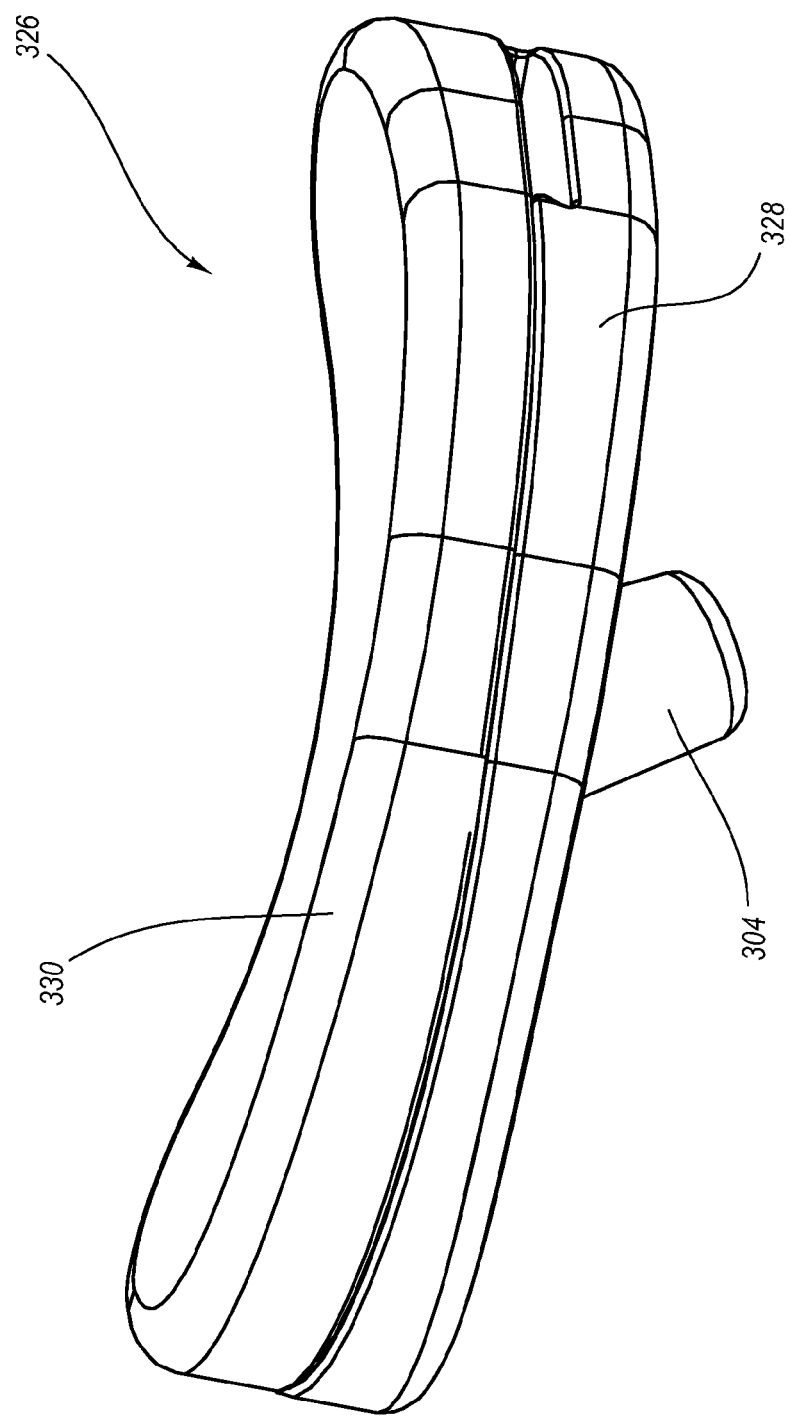
FIG. 14 is a perspective view of another alternative embodiment of a condylar implant.

In yet another alternative embodiment, depicted in FIG. 14 is a condylar implant 326. Like elements between condylar implants 300 and 326 are identified by like reference characters. In contrast to condylar implant 300 which is fixed and rigid, condylar implant 326 is mobile. Specifically, condylar implant 326 comprises a lower bearing plate 328 from which stem 304 projects and an upper bearing plate 330 that is slidably mounted on lower bearing plate 328.

Figure 15A:
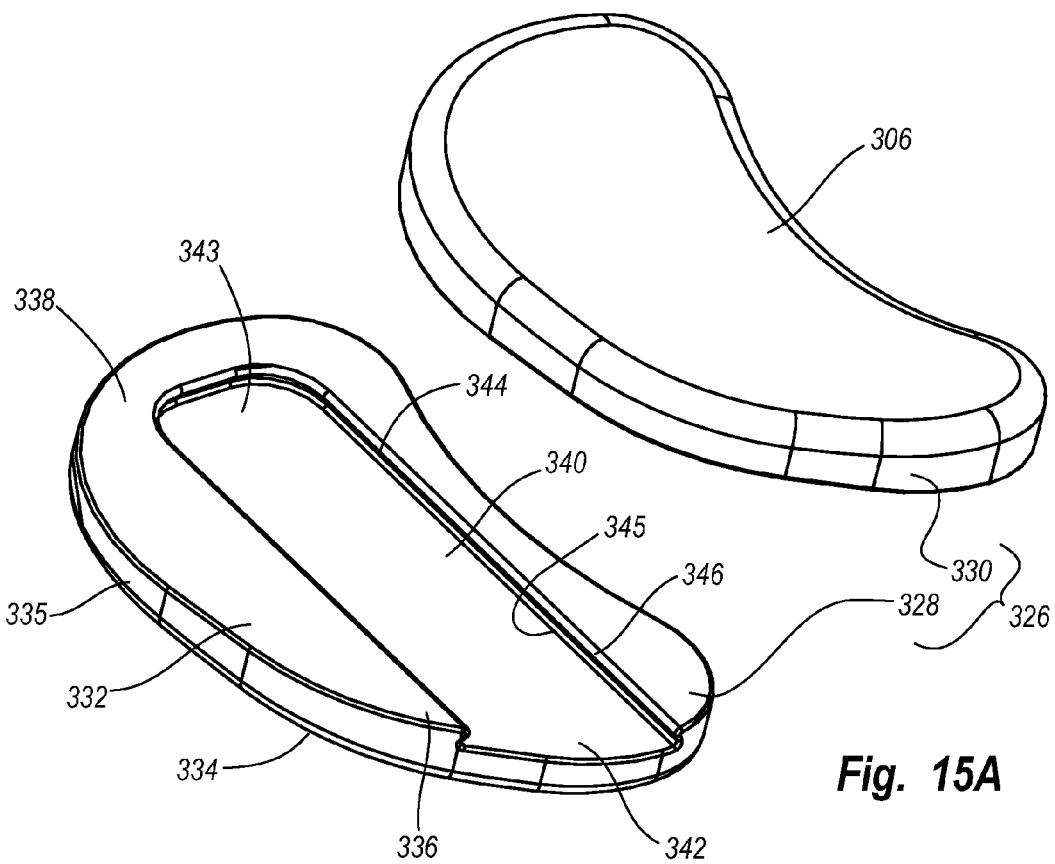
FIG. 15A is a top exploded perspective view of the condylar implant shown in FIG. 14.
Figure 15B:
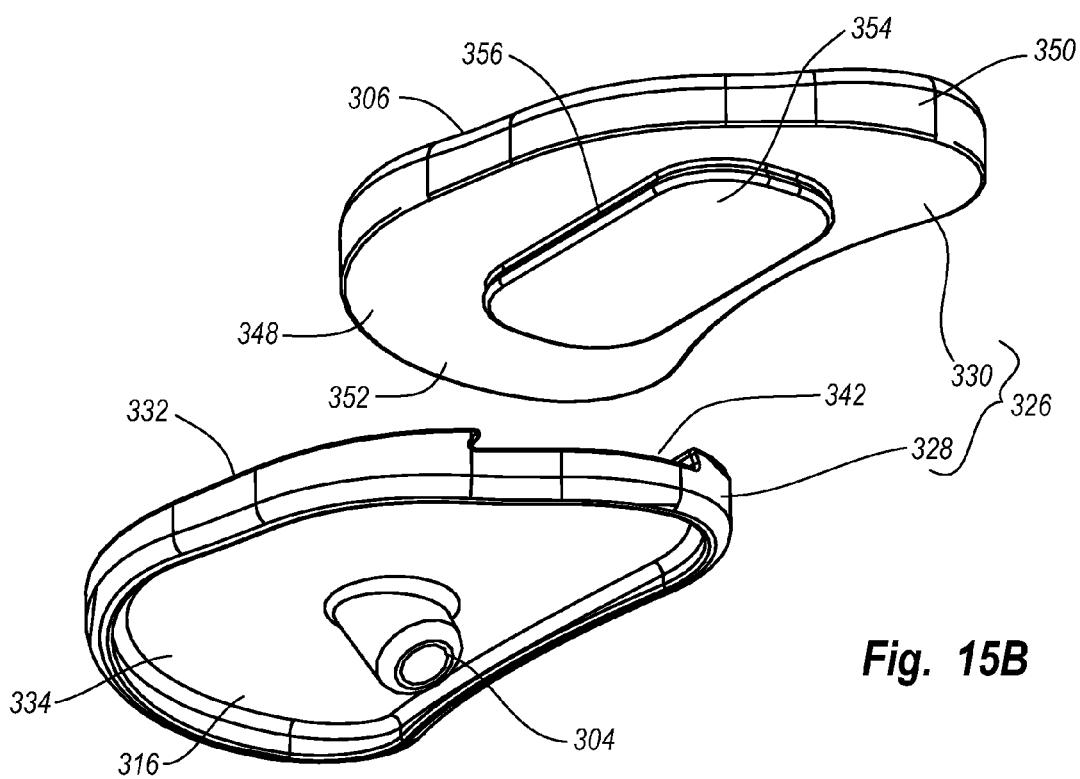
FIG. 15B is bottom exploded perspective view of the condylar implant shown in FIG. 15A.

As depicted in FIGS. 15A and B, lower bearing plate 328 has a top surface 332 and an opposing bottom surface 334 with a perimeter edge 335 extending therebetween. Pocket 316 is formed on bottom surface 334 to receive inlay 320. Top surface 332 is substantially flat or inwardly arched and extends between an anterior end 336 and a posterior end 338. A track 340 is recessed on top surface 332. Track 340 has an open mouth extending through perimeter edge 335 at anterior end 336 and longitudinally extends toward posterior end 338. Track 340 is bounded by a substantially flat floor 343 having a sidewall 344 upstanding therefrom. Sidewall 344 comprises a recess groove 345 which extends along floor 343 and an outwardly projecting lip 346 which projects along top surface 332. As such, the opposing sidewalls 344 of track 340 form a mortis.

Upper bearing plate 330 comprises top articular surface 306 and a bottom surface 348 which each extend between an anterior end 350 and an opposing posterior end 352. Bottom surface 348 has a configuration substantially congruent to top surface 332 of lower bearing plate 328. Projecting from bottom surface 348 is an elongated key 354 which extends from toward anterior end 350 to toward posterior end 352. Key 354 has a sidewall 356 that is substantially complementary to sidewall 344 of tack 340 such that key 354 forms a tenon that can slide into track 340 from mouth 342. In this position key 354 can freely slide along track 340 but is prevented from vertically separating from track 340.

During use, upper bearing plate 330 can slide posterior-anterior on lower bearing plate 328 as the femoral condyle rotates on top articular surface 306. This ability of upper bearing plate 330 to slide minimizes high stress points between the femoral condyle and upper bearing plate, thereby minimizing wear. Furthermore, because bearing plates 328 and 330 slide against each other on congruent surfaces, both of bearing plates 328 and 330 can be comprised of metal without producing undue wear. In other embodiments, bearing plates 328 and 330 can be comprised of plastics, ceramics, or composites of different materials. In addition, bearing plates 328 and 330 can be made of the same or different materials.

Figure 16A:
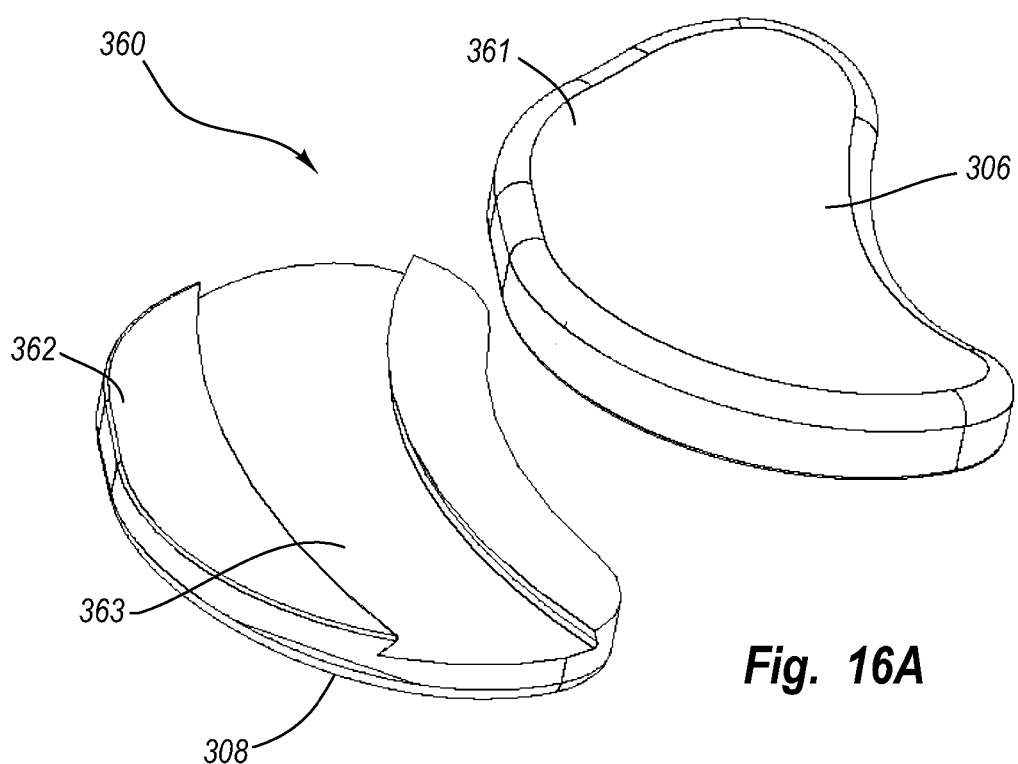
FIG. 16A is a top exploded perspective view of an alternative condylar implant.
Figure 16B:
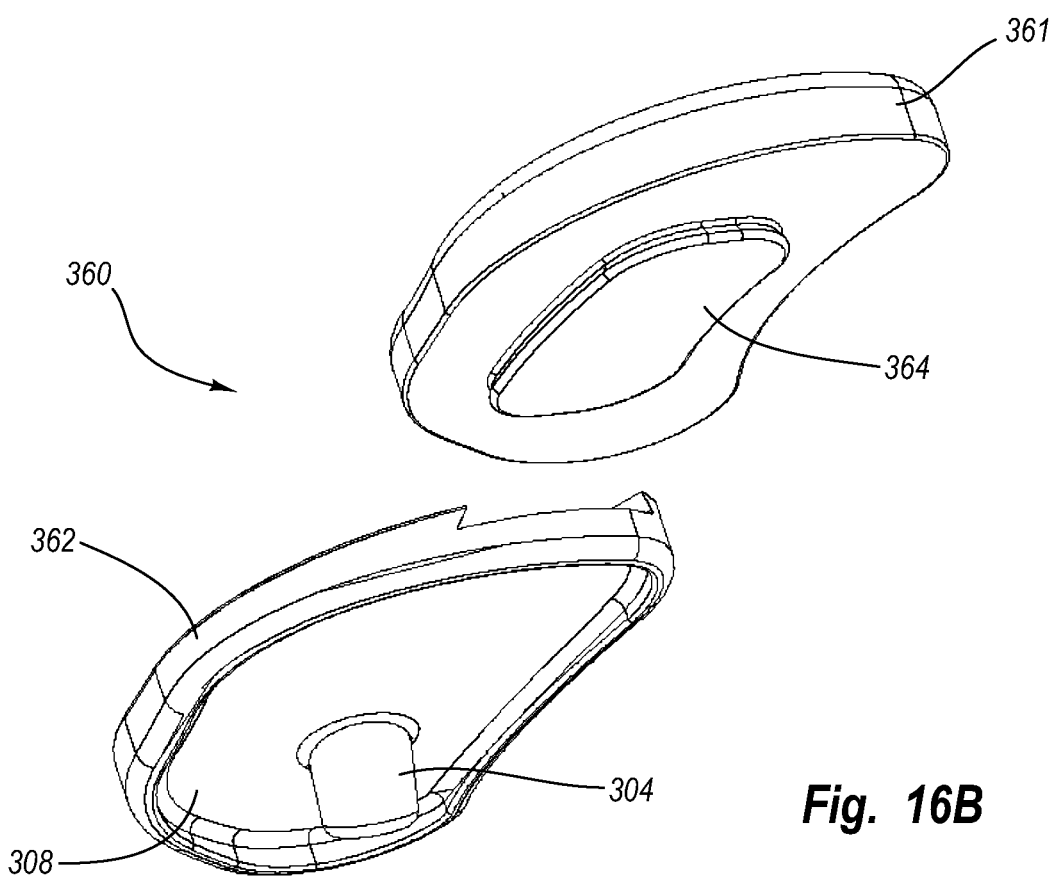
FIG. 16B is bottom exploded perspective view of the condylar implant shown in FIG. 16A.

Although key 354 and track 340 are shown as being linear, in alternative embodiments they can be congruently curved to more naturally correspond to the bending movement of the knee. For example, depicted in FIGS. 16A and B is another alternative embodiment of a condylar implant 360 which includes an upper bearing plate 361 and a lower bearing plate 362. In this embodiment, lower bearing plate 362 includes a track 363 that is curved along the length thereof. Upper bearing plate 361 includes an elongated key 364 having a curve complementary to track 363 such that key 364 can freely slide within track 363. As previously discussed, key 364 and track 363 can also be arched or curved in a vertical plane.

The present invention also provides means for connecting a fastener to the bottom surface of the bearing plate of a condylar implant. Examples of such means include stem 304 with threaded socket 312 or the other alternatives to threaded socket 312 as discussed above. Other examples of such means comprise the formation of threaded socket 312 directly on a bearing plate as depicted in FIG. 13. In other alternatives, the threads of socket 312 can be replaced with barbs, bayonet connectors, adhesive, or other alternative forms of connectors.

Figure 17:
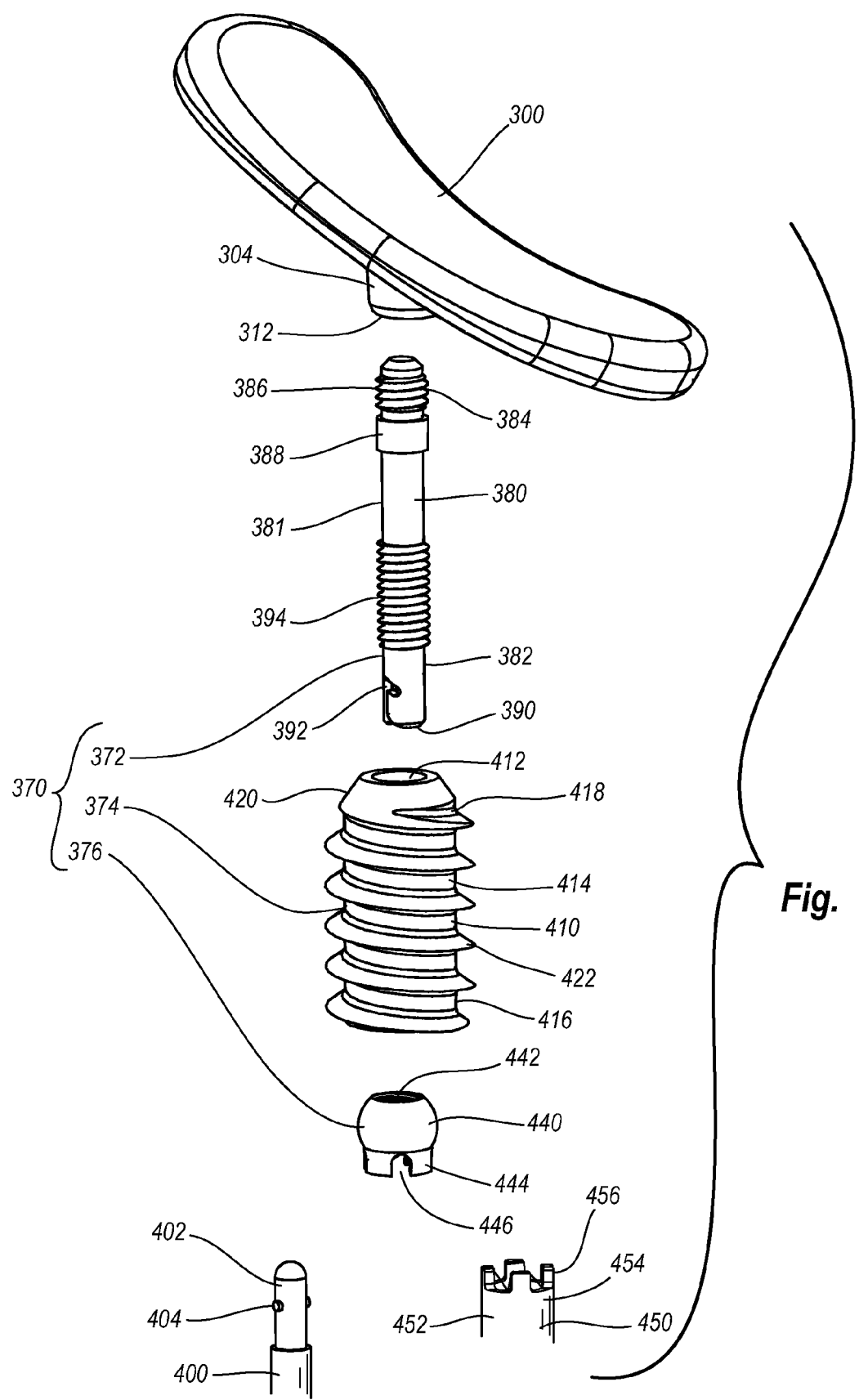
FIG. 17 is an exploded view of an anchor assembly for securing a condylar implant to the tibia shown in FIG. 10.

Depicted in FIG. 17 is one embodiment of an anchor assembly 370 used to secure condylar implant 300 to tibia 12. Anchor assembly 370 comprises a fastener 372, a bone anchor 374, and a crown nut 376. Fastener 372 comprises an elongated shaft 380 having an exterior surface 381 extending between a proximal end 382 and an opposing distal end 384. In one embodiment, fastener 372 has a length greater than 8 mm and more commonly greater 15 mm. Other dimensions can also be used.

Formed at distal end 384 of shaft 380 are threads 386 that are configured to threadedly mate with threaded socket 312 of stem 304. Outwardly projecting proximal of threads 386 is an annular flange 388 which functions as a stop when fastener 372 is threaded into stem 304. Recessed into proximal end 382 is a socket 390. A pair of opposing bayonet slots 392 longitudinally extend through the sidewall bounding socket 390. Finally, encircling and radially outwardly projecting from exterior surface 381 between proximal end 382 and flange 388 are engagement threads 394.

Figure 18:
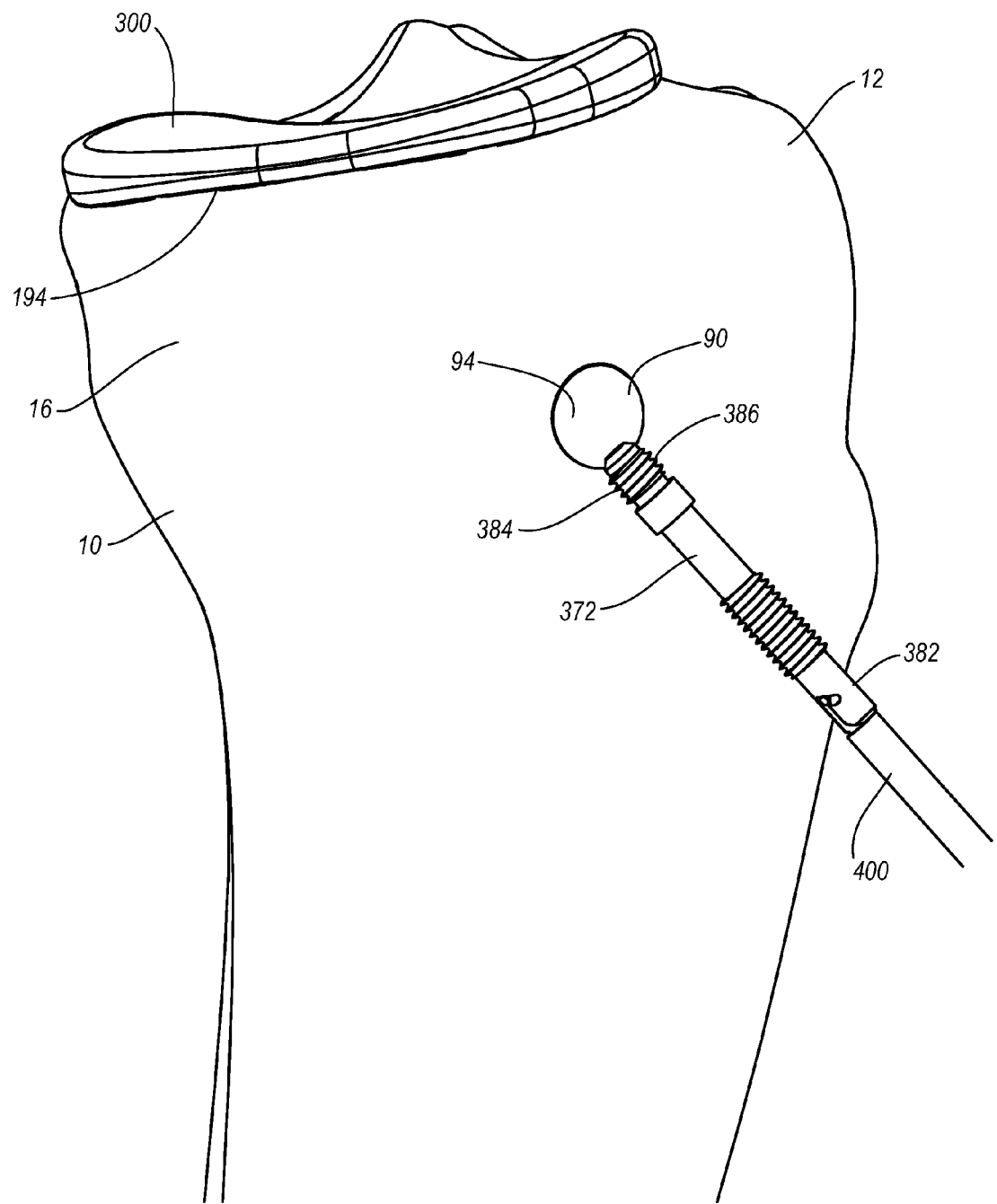
FIG. 18 is a side view of the fastener of the anchor assembly shown in FIG. 17 being secured to the condylar implant positioned on the tibia.

As depicted in FIG. 18, condylar implant 300 is mounted within recess 194 such that stem 304 is received within distal end 96 of tunnel 90. A fastener driver 400 has a distal head 402 (FIG. 17) that is configured to be received within socket 390 of fastener 372. A pair of opposing bayonet prongs 404 project from head 402 and are configured to mate within bayonet slots 392. With fastener driver 400 secured to proximal end 382 of fastener 372, fastener driver 400 is used to advance distal end 384 into tunnel 90 through proximal end 94. Fastener 372 is advanced through tunnel 90 so that threads 386 are received within socket 312 of stem 304. Fastener driver 400 is then rotated so that fastener 372 is threaded into stem 304.

Next, bone anchor 374 is secured within tunnel 90. In one embodiment, a tap, not shown, is used to initially thread interior surface 92 of tunnel 90. This can be accomplished before or after positioning of fastener 372. Alternatively, bone anchor 374 can be self-tapping.

As depicted in FIG. 17, bone anchor 374 comprises a tubular body 410 having a substantially cylindrical configuration. Body 410 includes an interior surface 412 and an exterior surface 414 that each extend between a proximal end 416 and an opposing distal end 418. Distal end 418 includes a tapered nose 420. Encircling and radially outwardly projecting from exterior surface 414 are one or more helical threads 422. As mentioned above, the threads can be conventional or self-taping. In alternative embodiments, threads 422 can be replaced by ridges, barbs, or other bone engaging structures used in conventional bone anchors. Bone anchor 374 can be formed of a biocompatible metal, a bioabsorbable polymer, a bioactive ceramic, or any other desired material.

Figure 19:
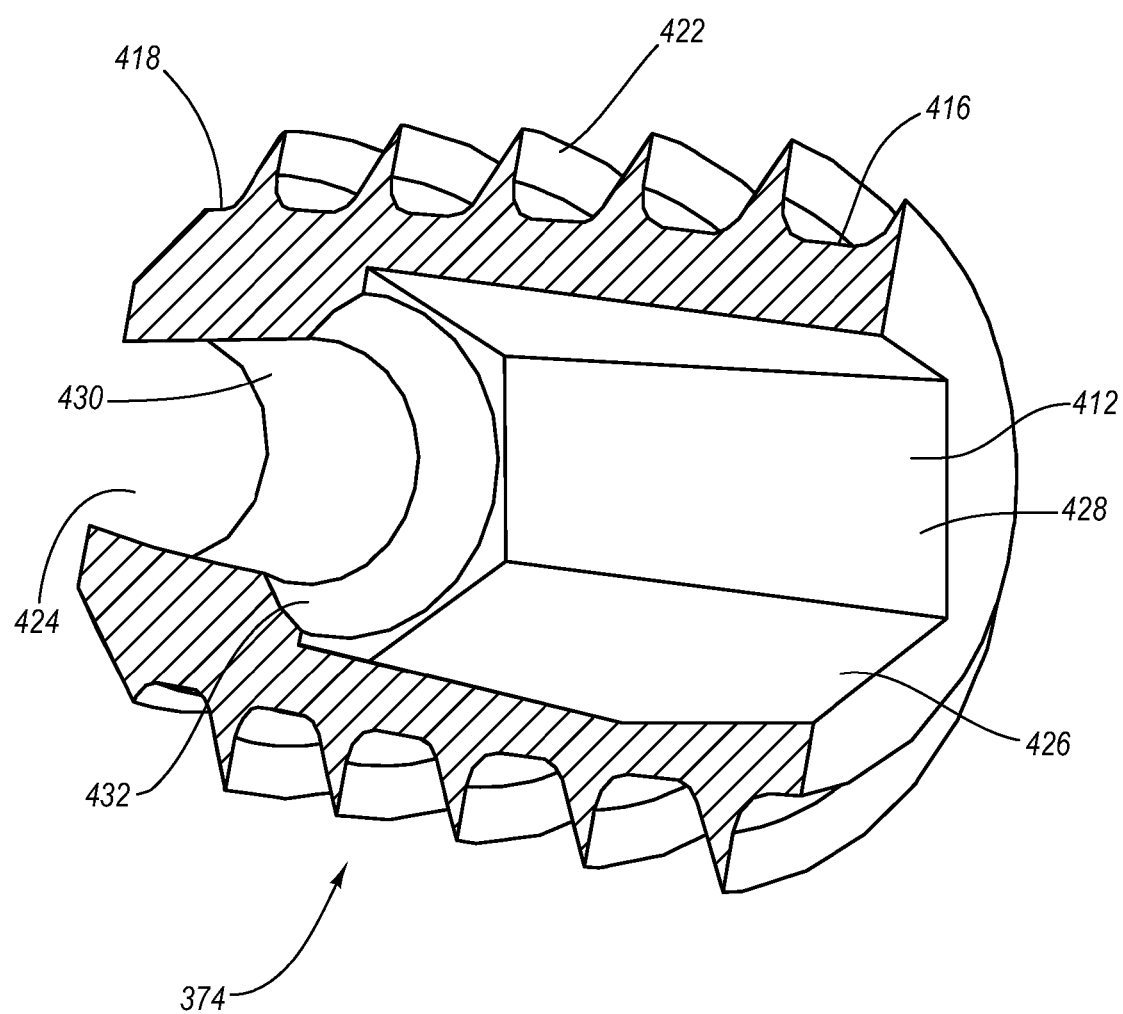
FIG. 19 is a cross sectional perspective view of the bone anchor of the anchor assembly shown in FIG. 17.

As depicted in FIG. 19, interior surface 412 bounds a channel 424 longitudinally extending through bone anchor 374. Interior surface 412 comprises a first sidewall 426 extending from proximal end 416, a second sidewall 430 extending from distal end 418, and an annular shoulder 432 extending between first sidewall 426 and second sidewall 430. First sidewall 426 has a maximum diameter that is greater than the maximum diameter of second sidewall 430. As such, shoulder 432 is tapered so as to constrict from first sidewall 426 to second sidewall 430. First sidewall 426 bounds a socket 430 which is configured to receive a tool for rotation of bone anchor 374. As such, first sidewall 426 has a non-circular transverse cross section. In typical embodiments, first sidewall 426 has a polygonal transverse cross section.

Figure 20:
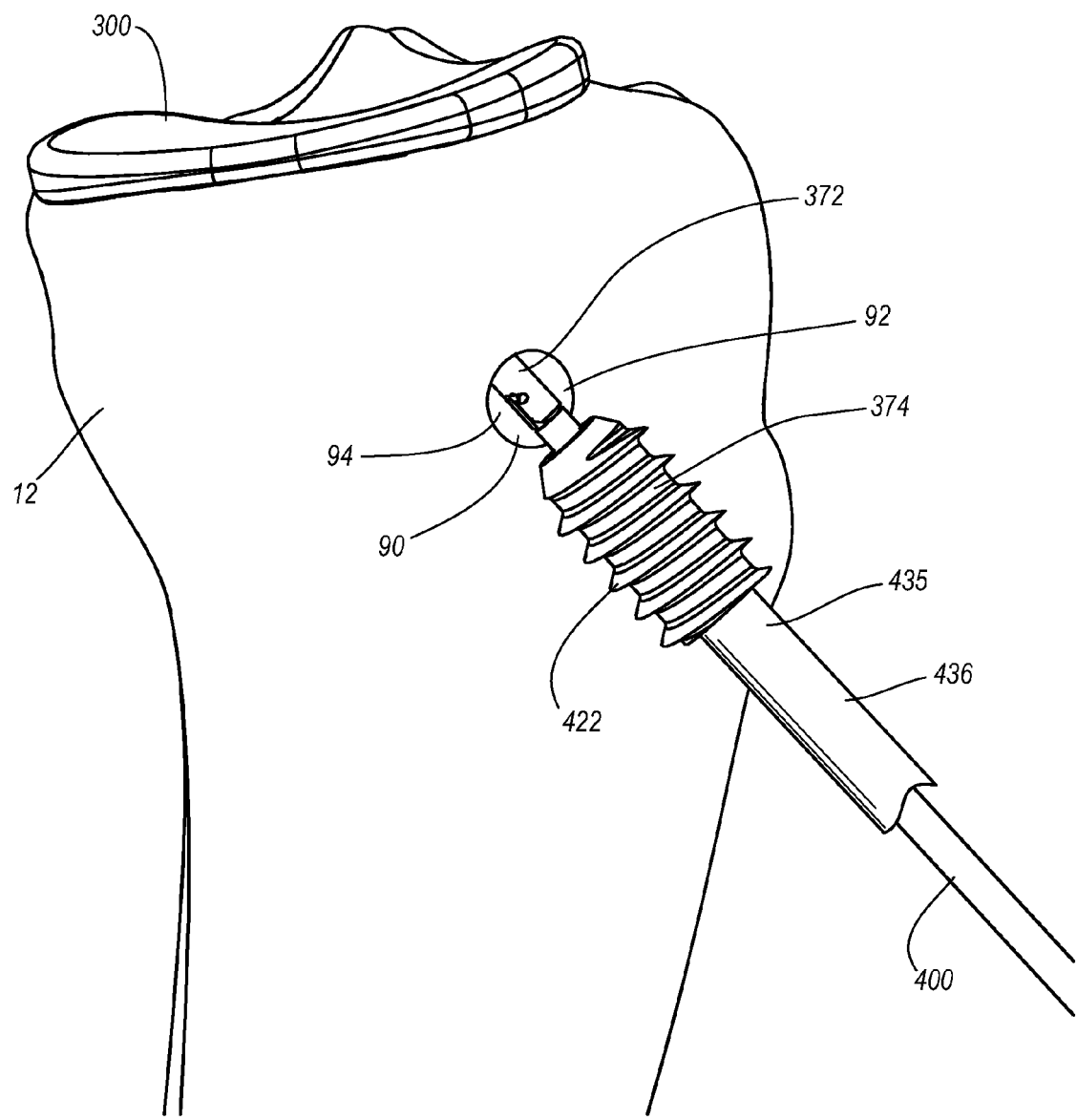
FIG. 20 is a side view of the bone anchor shown in FIG. 19 being FIG. 17 to the tibia shown in FIG. 18.

Turning to FIG. 20, a distal end 435 of a tubular anchor driver 436 is received within engagement socket 438 of bone anchor 374. Distal end 435 has a polygonal configuration complementary to socket 438 such that rotation of anchor driver 436 rotates bone anchor 364. Bone anchor 374 and anchor driver 436 are passed over the proximal end of fastener driver 400 and advanced to proximal end 94 of tunnel 90. By rotating anchor driver 436, bone anchor 374 is screwed into tunnel 90 using fastener driver 400 as a guide. Bone anchor 374 is sized so that threads 422 engage with interior surface 92 of tunnel 90, thereby securing bone anchor 374 to tibia 12 within tunnel 90. Bone anchor 374 is advanced so that bone anchor 374 encircles engagement threads 394 of fastener 372. Using fastener driver 400 as a guide for bone anchor 374 helps to concentrically dispose bone anchor 374 around fastener 372.

Once bone anchor 374 is positioned, anchor driver 436 is removed and crown nut 376 is positioned. As depicted in FIG. 17, crown nut 376 comprises a rounded head 440 having a threaded bore 442 extending therethrough. Projecting from head 440 are a plurality of spaced apart prongs 444 having notches 446 formed therebetween. Crown nut 376 is configured to mate with a nut driver 450. Nut driver 450 comprises a tubular shaft 452 that terminates at a distal end 454. Projecting from distal end 454 are a plurality of spaced apart prongs 456. Prongs 456 are configured to mate with crown nut 376 by being received within notches 446. In this mated configuration, rotation of nut driver 450 facilitates rotation of crown nut 376.

Figure 21:
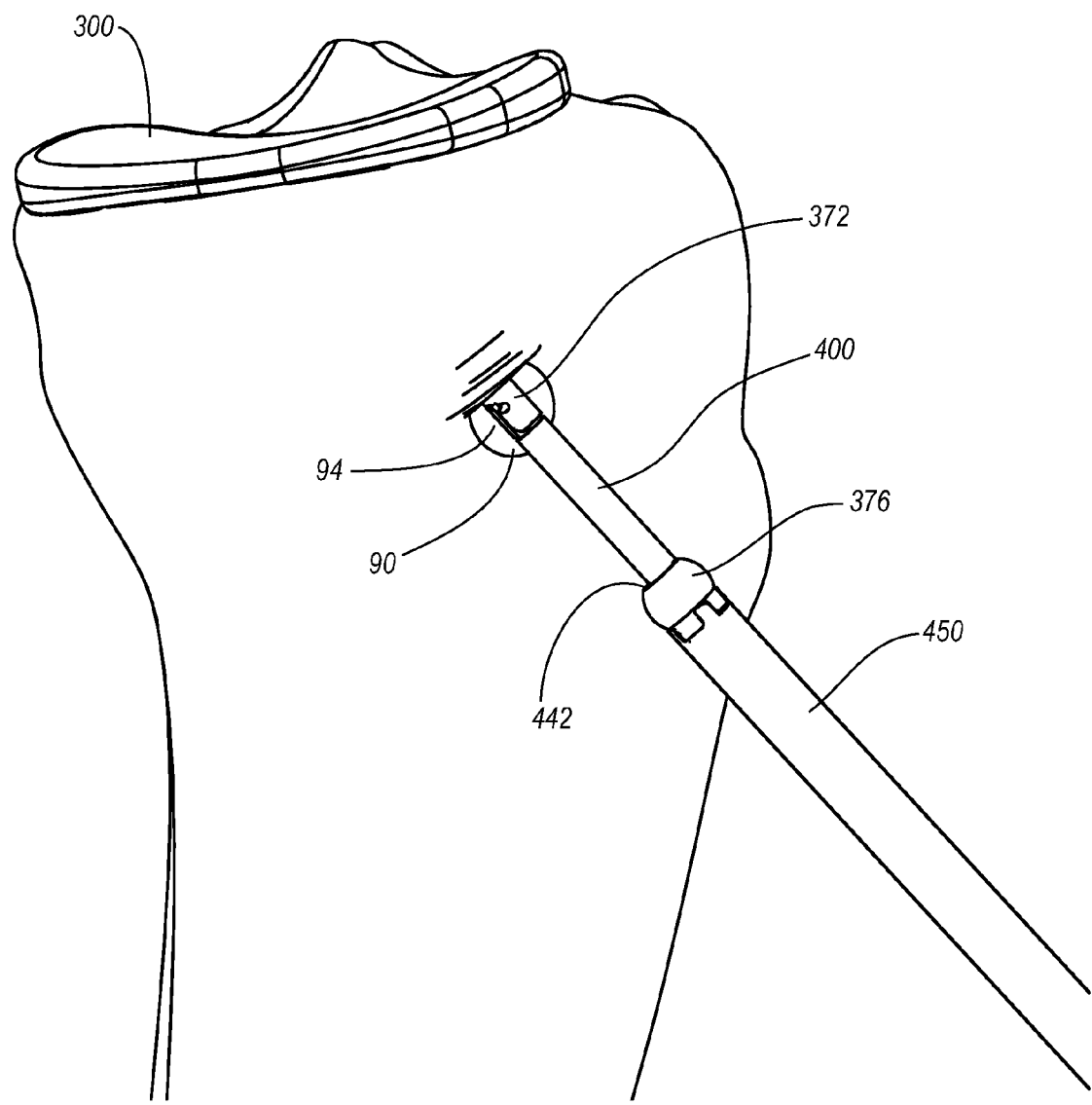
FIG. 21 is a side view of a crown nut of the anchor assembly shown in FIG. 17 being mounted to the fastener shown in FIG. 18.

Turning to FIG. 21, with crown nut 376 mounted on nut driver 450, crown nut 376 and nut driver 450 are passed over the proximal end of fastener driver 400. Nut driver 450 is used to advance crown nut along fastener driver 400, into tunnel 90, and over fastener 372. Threaded bore 442 of crown nut 376 is configured to threadedly mate with engagement threads 394 on fastener 372. Accordingly, once crown nut 376 is advanced over fastener 372 to engagement threads 394, nut driver 450 is rotated causing crown nut 376 to threadedly engage with engagement threads 394.

Figure 22:
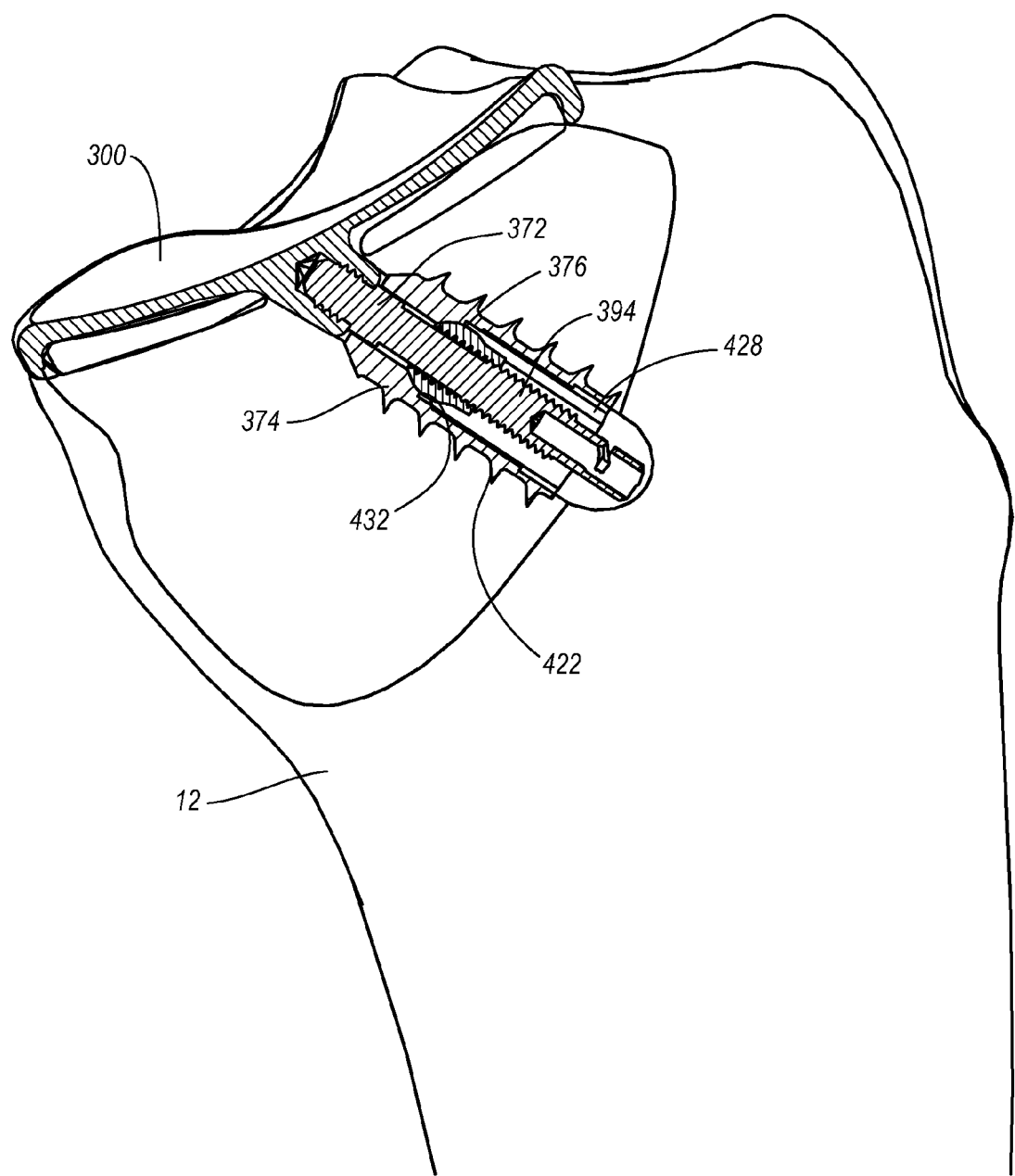
FIG. 22 is a cross sectional side view of the assembled anchor assembly shown in FIG. 17 securing the condylar implant to the tibia.

As depicted in FIG. 22, socket 428 of bone anchor 374 is larger than head 440 of crown nut 376 such that crown nut 376 can freely pass therethrough. Shoulder 432, however, constricts to a diameter smaller than the diameter of head 440 of crown nut 376. Accordingly, crown nut 376 is advanced along fastener 372 by engaging with threads 394 until head 440 of crown nut 376 biases against shoulder 432 of bone anchor 374. Tightening crown nut 376 against shoulder 432 produces tension on fastener 376 which tightly secures condylar implant 300 against tibia 12.

In one embodiment, engagement threads 394 on fastener 372 rotate in a direction opposite threads 422 on bone anchor 374. For example, engagement threads 394 can be right-hand threads while threads 422 are left-hand threads. As a result, rotation of crown nut 376 against bone anchor 374 does not cause bone anchor 364 to rotate concurrently. Furthermore, once crown nut 376 is initially positioned, nut driver 450 is removed. Anchor driver 436 can then be repositioned over fastener driver 400 so as to engage with bone anchor 374. Anchor driver 436 can then be used to back bone anchor 374 a distance back toward proximal end 94 of tunnel 90. In so doing, fastener 372 is further tensioned so as to increase the force securing condylar implant 300 on tibia 12. Again, because threads 394 and threads 422 rotate in opposite directions, backing bone anchor 374 does not cause crown nut 376 to unscrew.

Finally, once crown nut 376 and bone anchor 374 are positioned in their final state, fastener driver 400 is removed from fastener 372. Closing procedures for the tissue are then performed.

Figure 23:
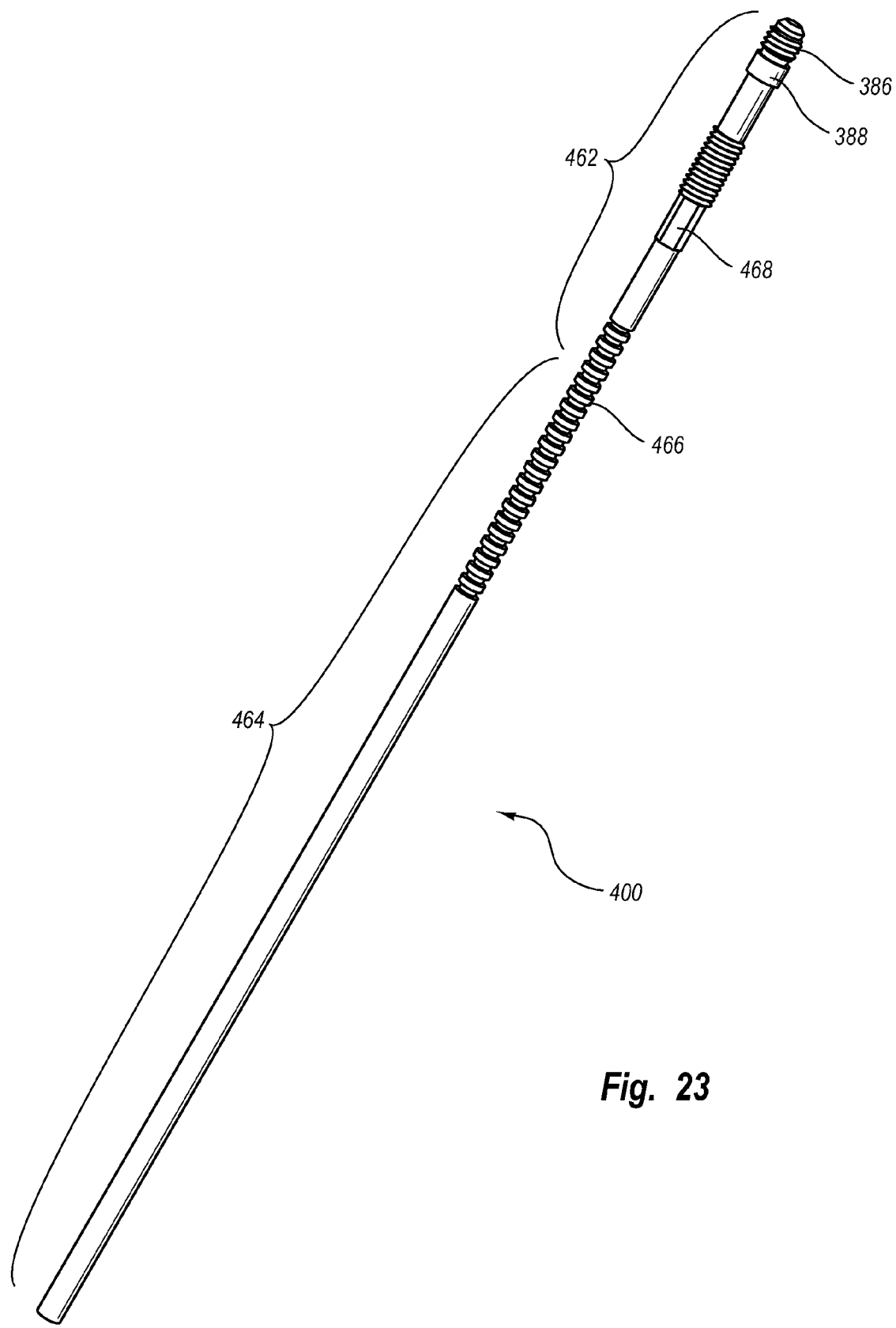
FIG. 23 is a perspective view of an alternative embodiment of the fastener shown in FIG. 17.

As discussed above, fastener driver 400 is useful as a guide in directing placement of bone anchor 374 and crown nut 376. In contrast to being separately connected to fastener 372, in one alternative embodiment the fastener driver can be integrally formed with fastener 372. For example, depicted in FIG. 23 is a fastener system 460. Fastener system 460 includes a fastener 462 and an elongated drive rod 464 integrally formed with fastener 462. Like elements between fasteners 372 and 462 are identified by like reference characters. As with fastener 372, fastener 462 includes flange 388 and threads 386 and 394. Formed proximal of threads 394 is a mating region 468. Mating region has a polygonal or other non-circular transverse cross section. As such removal or further tightening of fastener 462 can be accomplished by passing a tubular driver over fastener 462 so as to engage with mating region 468.

In contrast to socket 390 of fastener 372, fastener 462 is integrally formed with drive rod 464. To facilitate separation of drive rod 464 from fastener 462, a plurality of annular breaking grooves 466 encircle fastener system 460 at spaced apart locations along the junction between fastener 462 and drive rod 464.

Fastener system 460 is used in substantially the same manner as fastener 372 and fastener driver 400. However, once bone anchor 374 and crown nut 376 are finally positioned, fastener 462 and drive rod 464 are separated by breaking fastener system 460 at a annular breaking grooves 466 located adjacent to proximal end 94 of tunnel 90.

Figure 24:
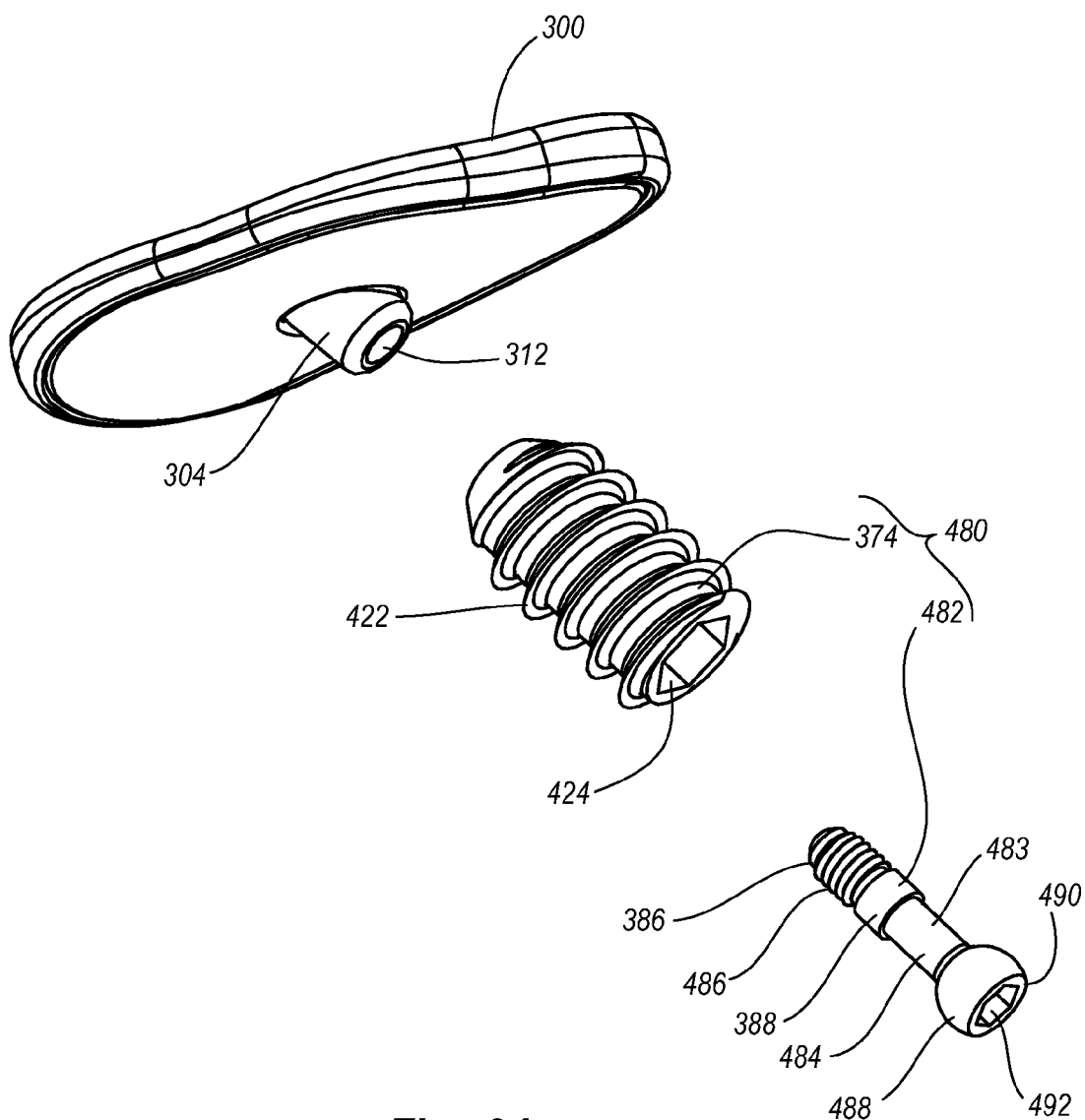
FIG. 24 is an alternative embodiment of an anchor assembly.

It is appreciated that the anchor assembly for condylar implant 300 can have a variety of different configurations. For example, depicted in FIG. 24 is an alternative embodiment of an anchor assembly 480. Anchor assembly 480 includes bone anchor 374, as discussed above, and a fastener 482. Like elements between fasteners 372 and 482 are identified by like reference characters. Fastener 482 includes a shaft 483 having a proximal end 484 and an opposing distal end 486. Mounted at or toward distal end 486 are threads 386 and flange 388 as discussed above. Mounted at proximal end 484 is an enlarged rounded head 488 that terminates at an end face 490. Recessed within end face 490 is a socket having a polygonal or other non-circular configuration. It is noted that head 488 has a maximum diameter that is smaller than the diameter of socket 424 of bone anchor 374 but larger than the minimum diameter of shoulder 432 of bone anchor 374. As such, head 488 seats against shoulder 432 when passed through bone anchor 374.

Figure 25:
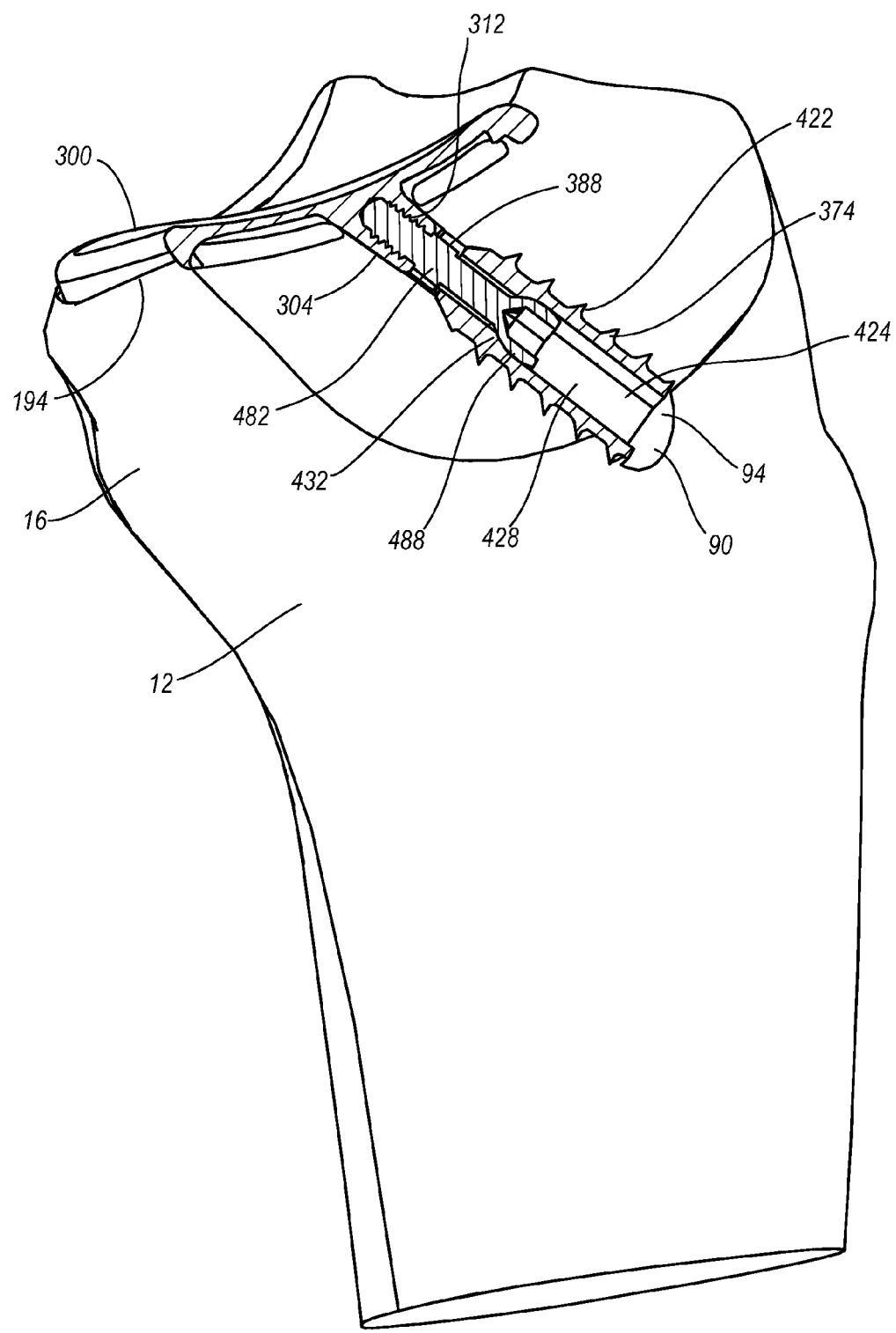
FIG. 25 is a cross section side view of the anchor assembly shown in FIG. 24 securing a condylar implant to a tibia.

Turning to FIG. 25, in contrast to anchor assembly 370 where fastener 372 is initially positioned, in anchor assembly 480 bone anchor 374 is initially secured within tunnel 90 using anchor driver 436. Again, tunnel 90 can be pre-tapped or threads 422 on bone anchor 374 can be self-tapping. Once bone anchor 374 is positioned, a driver, not shown, is inserted within socket 492 of fastener 482. The driver is then used to advance distal end 486 of fastener 482 into tunnel 90, through channel 424 of bone anchor 374, and into socket 312 of condylar implant 300. The driver is then used to rotate fastener 482 so that threads 386 threadedly engage with socket 312. Fastener 482 is advanced into socket 312 until flange 388 contacts the end face of stem 304. The driver for fastener 482 is then removed.

Next, anchor driver 436 is inserted back into socket 428 of bone anchor 374. This can be accomplished by passing anchor driver 436 over the driver for fastener 482 or by first removing the driver for fastener 482. Anchor driver 436 is then used to back bone anchor 374 a distance toward proximal end 94 of tunnel 90. In so doing, shoulder 432 of bone anchor 374 biases against head 488 of fastener 482, thereby tensioning fastener 482 so as to securely bias condylar implant 300 against tibia 12. It is appreciated that threads 386 of fastener 482 and threads 422 of bone anchor 374 rotate in opposite directions so that the backing of bone anchor 374 does not unscrew fastener 482 from condylar implant 300.

It is appreciated that in alternative embodiments the various threaded connections used in association with the anchor assemblies can be replaced with bayonet connections, expanding collets, press fit barb connections, and other conventional connections commonly used in place of thread connections.

By using the above discussed condylar implants and anchor assemblies with the corresponding methods, it is appreciated that the condylar implants can be securely mounted to tibia 12 using procedures that are minimally invasive.

Figure 26A:
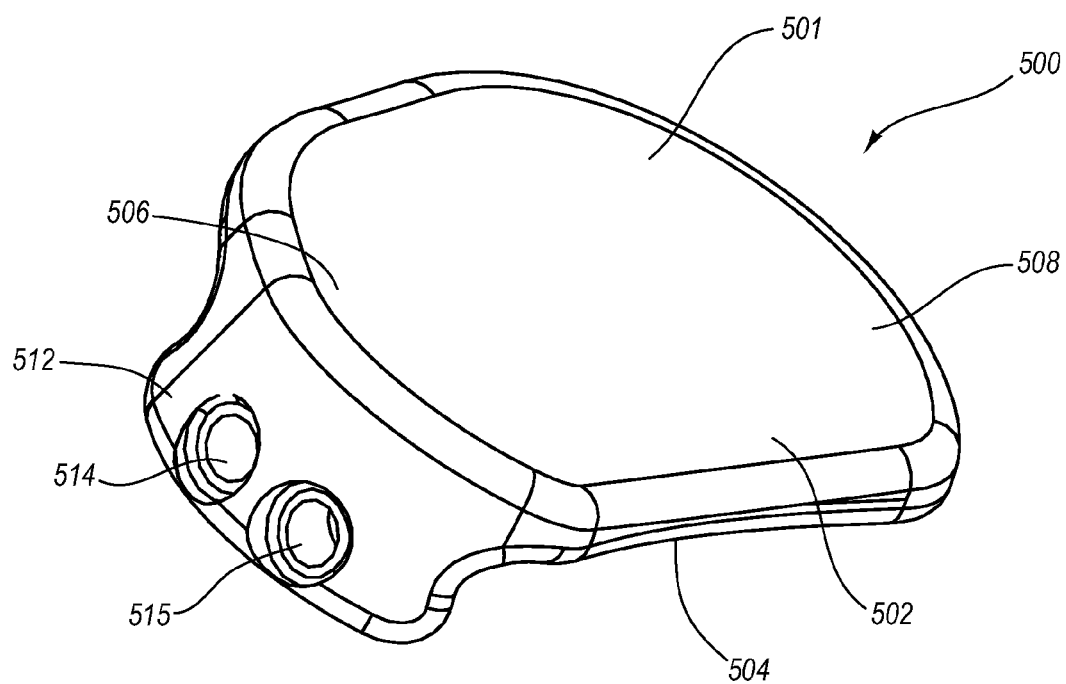
FIG. 26A is a top perspective view of an alternative embodiment of a condylar implant.
Figure 26B:
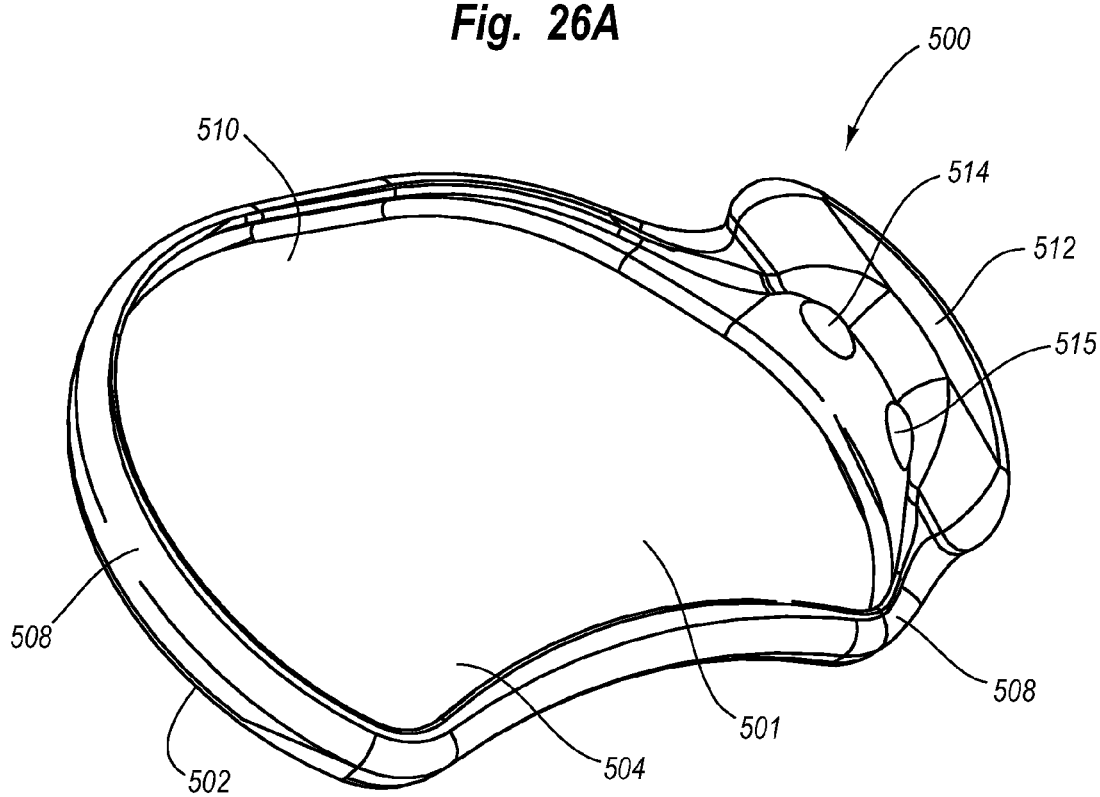
FIG. 26B is a bottom perspective view of the condylar implant shown in FIG. 26A.

In other alternative embodiments, it is also appreciated that various condylar implants can be designed for implanting in a minimally invasive procedure which may or may not require the formation of a tunnel through tibia 12. For example depicted in FIGS. 26A and B is an alternative embodiment of a condylar implant 500 incorporating features of the present invention. Condylar implant 500 comprises a bearing plate 501 having a top articular surface 502 and an opposing bottom surface 504 which each extend between an anterior end 506 and a posterior end 508. Although not required, in the embodiment depicted, a pocket 510 is formed on bottom surface 504 to receive an inlay of bone ingrowth material (not shown).

Downwardly extending from bottom surface 504 at anterior end 506 is a mounting flange 512. A pair of spaced apart holes 514 and 515 extend through mounting flange 512.

During use, medial facet 24 is resected so as to received condylar implant 500. The resection can be preformed at least in part using the procedures as discussed above by forming tunnel 90. Alternatively, other conventional techniques can be used to resect medial facet 24 without the formation of tunnel 90. In either embodiment, a portion of the medial or anterior face of tibia 12 is also resected so as to receive mounting flange 512. Once mounting flange 512 is positioned, screws are advanced through holes 514 and 515 into the lateral, medial, or anterior side of tibia 12 so as to directly screw condylar implant 500 to tibia 12.

In an alternative embodiment, it is also appreciated that stem 304 of condylar implant 300 can be mounted on bottom surface 504 of condylar implant 500. In this embodiment, condylar implant 500 can be mounted both through the use of stem 512, as discussed above, and by screws passing through holes 514 and 515.

Figure 27A:
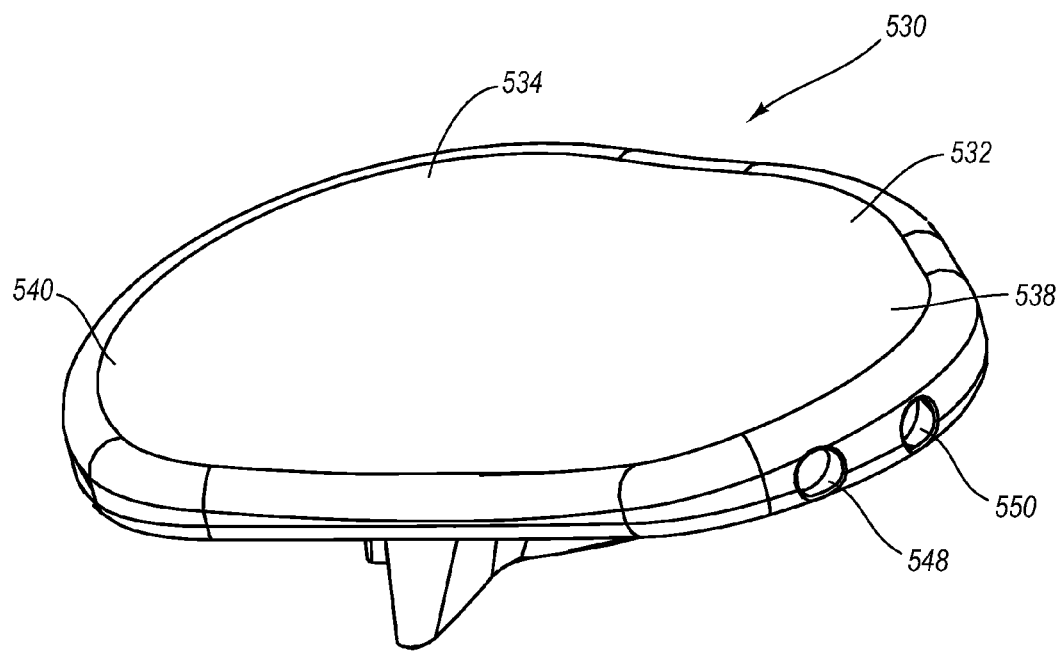
FIG. 27A is a top perspective view of another alternative embodiment of a condylar implant.
Figure 27B:
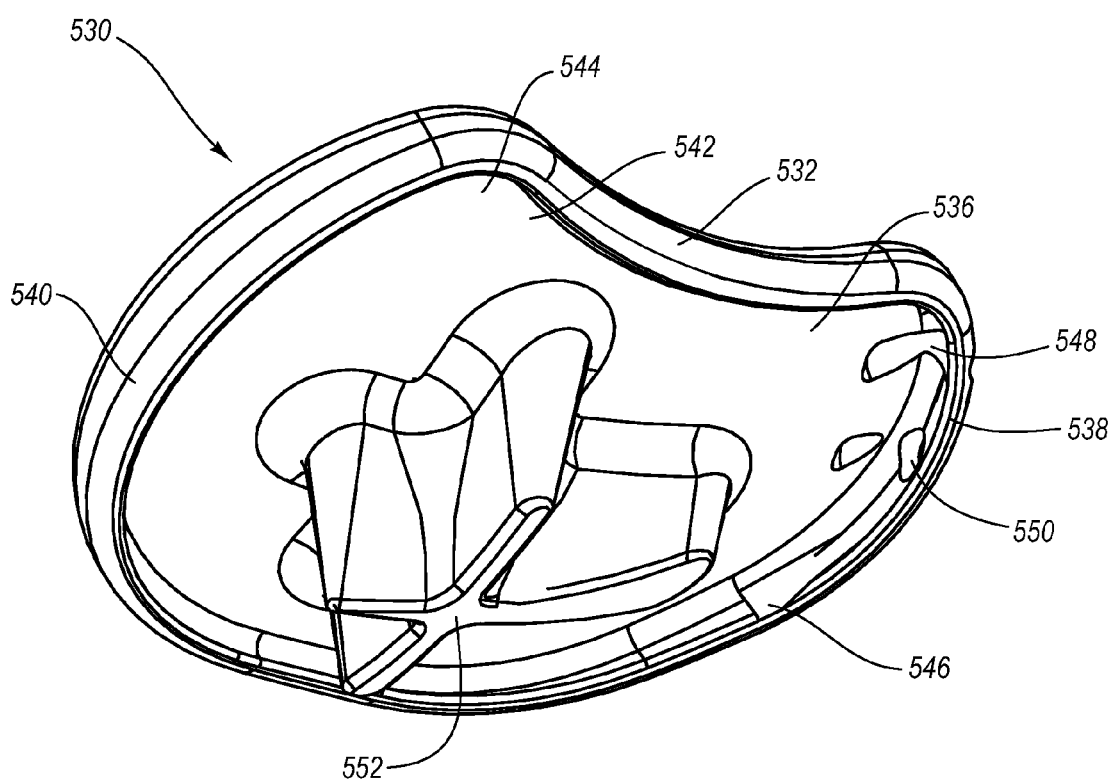
FIG. 27B is a bottom perspective view of the condylar implant shown in FIG. 7A.

Depicted in FIGS. 27A and B is still another alternative embodiment of a condylar implant 530. Condylar implant 530 comprises a bearing plate 532 having a top articular surface 534 and an opposing bottom surface 536 which each extend between an anterior end 538 and a posterior end 540. A pocket 542 is formed on bottom surface 536. Pocket 542 is bounded by a floor 544 and a sidewall 546 upstanding around the perimeter of floor 544. Extending through sidewall 546 at anterior end 538 are a pair of spaced apart holes 548 and 550.

Centrally projecting from floor 544 is a post 552 having substantially t-shaped configuration. In alternative embodiments post 552 can be any desired configuration. Pocket 542 is designed to partially receive an inlay of bone ingrowth material (not shown) so as to encircle post 552.

During use, a slot complementary to post 552 is formed on the resected facet of the tibia. Condylar implant 530 is then positioned on the resected facet so that post 552 is received within the slot. Screws are then passed through 550 and 552 at a downward angle so as to penetrate into the tibia. Here it is appreciated that the inlay of bone ingrowth material will also need to have corresponding holes extending therethrough so that the screws can pass through the bone ingrowth material into the tibia.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A condylar implant for mounting on the proximal end of a tibia, the condylar implant comprising:
a bearing plate having a top articular surface and an opposing bottom surface, the top articular surface being adapted to mate with a femoral condyle;
a stem downwardly projecting from the bottom surface of the bearing plate, the stem having a proximal end formed on the bottom surface of the bearing plate and an opposing distal end that is spaced apart from the bottom surface of the bearing plate with a central longitudinal axis extending through the stem between the proximal end and the distal end thereof, the stem being oriented so that the central longitudinal axis extending from the proximal end of the stem intersects with and passes through the bearing plate adjacent to the proximal end of the stem and an inside angle is formed between the central longitudinal axis of the stem and the bottom surface of the bearing plate in a range between about 30° to about 80°, the stem and the bearing plate being fabricated as a monolithic piece of material so that there is no mechanical connection removably coupling the stem to the bearing plate; and
means for connecting a fastener to the stem.

2. A condylar implant as recited in claim 1, wherein the bearing plate comprises:
a lower bearing plate having the stem projecting therefrom; and
an upper bearing plate having the top articular surface formed thereon, one of the lower bearing plate and upper bearing plate having a track formed thereon while the other has a key that slidably rides within the track.

3. A condylar implant as recited in claim 2, wherein the key has the configuration of a tenon while the track comprises a mortis configured to slidably receive the tenon.

4. A condylar implant as recited in claim 1, further comprising:
the bottom surface of the bearing plate having a pocket formed thereon; and
an inlay being secured within the pocket.

5. A condylar implant as recited in claim 4, wherein the pocket and the inlay encircle the stem.

6. A condylar implant as recited in claim 1, wherein the means for connecting the fastener to the stem comprises a threaded socket formed on the stem.

7. A condylar implant as recited in claim 1, wherein the bearing plate has a maximum thickness in a range between about 2 mm to about 10 mm.

8. A condylar implant as recited in claim 1, wherein the stem has a length in a range between about 2 mm to about 6 mm.

9. A condylar implant as recited in claim 1, further comprising a mounting flange downwardly projecting from the bottom surface of the bearing plate at a perimeter edge of the bearing plate, the mounting flange bounding at least one hole extending therethrough.

10. A condylar implant as recited in claim 1, wherein the stem is oriented so that a distance from the bottom surface of the bearing plate to the central longitudinal axis at the distal end of the stem is greater than a distance from the bottom surface of the bearing plate to the central longitudinal axis at the proximal end of the stem.

11. A condylar implant as recited in claim 1, wherein the stem is oriented so that a substantially V-shaped notch is formed between the bottom surface of the bearing plate and an exterior surface of the stem.

12. A condylar implant system comprising:
a condylar implant comprising:
a bearing plate having a top articular surface and an opposing bottom surface, the top articular surface being adapted to mate with a femoral condyle;
a stem downwardly projecting from the bottom surface of the bearing plate; and
means for connecting a fastener to the stem;
a fastener mechanically engaging with the stem; and
a tubular bone anchor removably encircling at least a portion of the fastener, wherein the fastener has external threads that rotate in a first direction and the bone anchor has external threads that rotate in a second direction that is opposite of the first direction.

13. A condylar implant system as recited in claim 12, wherein the fastener comprises a shaft having threads formed thereon.

14. A condylar implant system as recited in claim 13, further comprising an enlarged head integrally formed on the shaft or an enlarged nut removably mountable on the shaft.

15. A condylar implant system as recited in claim 12, wherein the bone anchor has an interior surface bounding a channel extending between a first end and an opposing second end, the first end terminating at a first end face, the channel comprising a first channel portion extending from the first end, a second channel portion extending from the second end, and a radially inwardly projecting shoulder disposed between the first channel portion and the second channel portion.

16. A condylar implant system for use on the proximal end of a tibia, the system comprising:
    a condylar implant comprising a bearing plate having a top articular surface and an opposing bottom surface;
    an elongated fastener selectively mountable to the bottom surface of the bearing plate; and
    a tubular bone anchor removably encircling at least a portion of the fastener, the bone anchor having an interior surface bounding a channel extending between a first end and an opposing second end, the first end terminating at a first end face, the channel comprising a first channel portion extending from the first end, a second channel portion extending from the second end, and a radially inwardly projecting shoulder disposed between the first channel portion and the second channel portion, the bone anchor further comprising one or more threads or barbs formed on an exterior surface thereof.

17. A condylar implant system as recited in claim 16, wherein the condylar implant further comprises a stem projecting from the bottom surface of the bearing plate, the stem being configured to mate with the fastener.

18. A condylar implant system as recited in claim 16, wherein the fastener mounts to the bearing plate so as to form an inside angle between the fastener and the bottom surface of the bearing plate in a range between about 30° to about 80°.

19. A condylar implant system as recited in claim 16, wherein the bearing plate comprises:
    a lower bearing plate having the bottom surface formed thereon; and
    an upper bearing plate having the top articular surface formed thereon, one of the lower bearing plate and upper bearing plate having a track formed thereon while the other has a key that slidably rides within the track.

20. A condylar implant system as recited in claim 16, further comprising:
    the bottom surface of the bearing plate having at least one pocket formed thereon; and
    an inlay comprised of a porous bone ingrowth material being secured within the at least one pocket.

21. A condylar implant system as recited in claim 16, wherein the fastener comprises an elongated shaft having a length in a range between about 5 mm to about 15 mm.

22. A condylar implant system as recited in claim 16, wherein the fastener comprises an elongated shaft having an enlarged head integrally formed thereon.

23. A condylar implant system as recited in claim 16, further comprising an enlarged nut removably mountable to the fastener.

24. A condylar implant system as recited in claim 16, wherein the fastener has at least one helical thread that engages with the condylar implant and the bone anchor has at least one external helical thread, the helical thread of the bone anchor rotating in a direction opposite of the helical thread of the fastener.

25. A condylar implant system as recited in claim 16, wherein the fastener comprises a shaft having an enlarged head integrally formed thereon, the head being biased against the shoulder of the bone anchor.

26. A condylar implant system as recited in claim 16, further comprising an enlarged nut removably mounted on the fastener and biased against the shoulder of the bone anchor.

27. A condylar implant system as recited in claim 16, further comprising a drive rod integrally formed with the fastener, a plurality of spaced apart annular breaking grooves being formed at the intersection between the fastener and the drive rod.

28. A condylar implant system for use on the proximal end of a tibia, the system comprising:
    a condylar implant comprising a bearing plate having a top articular surface and an opposing bottom surface, a stem projecting from the bottom surface of the bearing plate;
    an elongated fastener configured to selectively mate with the stem;
    a tubular bone anchor removably encircling at least a portion of the fastener, the bone anchor having an exterior surface with at least one helical thread radially outwardly projecting therefrom; and
    a nut having a passage extending completely therethrough, the nut being removably threaded onto the fastener.

29. A condylar implant system as recited in claim 28, wherein the bearing plate and the stem comprise a unitary member that is fabricated from a single piece of material.

30. A condylar implant system for use on the proximal end of a tibia, the system comprising:
    a condylar implant comprising a bearing plate having a top articular surface and an opposing bottom surface;
    an elongated fastener having a first end and an opposing second end, the first end being removably threaded to the bottom surface of the bearing plate without extending through the bearing plate; and
    a nut having a passage extending completely therethrough, the nut being removably threaded onto the fastener from the second end of the fastener.

31. A condylar implant system as recited in claim 30, further comprising a tubular bone anchor removably encircling at least a portion of the fastener.

32. A condylar implant system as recited in claim 30, wherein the bone anchor has an exterior surface with at least one helical thread radially outwardly projecting therefrom.

33. A condylar implant system for use on the proximal end of a tibia, the system comprising:
    a condylar implant comprising a bearing plate having a top articular surface and an opposing bottom surface, the top articular surface being adapted to mate with a femoral condyle;
    a fastener comprising an elongated shaft having a first end and an opposing second end, the first end being removably mounted to the bottom surface of the bearing plate, an enlarged head being permanently fixed on the shaft or an enlarged nut being removably mountable onto the shaft; and
    a tubular bone anchor removably encircling at least a portion of the fastener, at least one or more threads or barbs being formed on an exterior surface of the bone anchor.

* * * * *